(12) United States Patent
Kyriazopoulou Panagiotopoulou et al.

(10) Patent No.: US 11,861,491 B2
(45) Date of Patent: Jan. 2, 2024

(54) DEEP LEARNING-BASED PATHOGENICITY CLASSIFIER FOR PROMOTER SINGLE NUCLEOTIDE VARIANTS (PSNVS)

(71) Applicant: Illumina, Inc., San Diego, CA (US)

(72) Inventors: Sofia Kyriazopoulou Panagiotopoulou, Redwood City, CA (US); Kai-How Farh, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 1095 days.

(21) Appl. No.: 16/578,210

(22) Filed: Sep. 20, 2019

(65) Prior Publication Data
US 2020/0019859 A1 Jan. 16, 2020

Related U.S. Application Data

(63) Continuation-in-part of application No. 16/160,903, filed on Oct. 15, 2018, now Pat. No. 10,423,861.
(Continued)

(51) Int. Cl.
| | |
|---|---|
| G16B 40/00 | (2019.01) |
| G06N 3/08 | (2023.01) |
| G06N 20/20 | (2019.01) |
| G06N 3/084 | (2023.01) |
| G06N 3/082 | (2023.01) |

(Continued)

(52) U.S. Cl.
CPC ............... G06N 3/08 (2013.01); G06N 3/082 (2013.01); G06N 3/084 (2013.01); G06N 20/20 (2019.01); G16B 40/00 (2019.02); G06N 3/044 (2023.01); G06N 3/045 (2023.01)

(58) Field of Classification Search
CPC ............................. G16N 40/10; G16B 40/00
See application file for complete search history.

(56) References Cited

U.S. PATENT DOCUMENTS

| | | |
|---|---|---|
| 6,060,033 A | 5/2000 | Cheng |
| 6,269,934 B2 | 7/2001 | Bjorkesten |

(Continued)

FOREIGN PATENT DOCUMENTS

| | | |
|---|---|---|
| CA | 2894317 A1 | 12/2016 |
| CN | 103679185 A | 3/2014 |

(Continued)

OTHER PUBLICATIONS

Ionita-Laza, I., McCallum, K., Xu, B., & Buxbaum, J. D. A spectral approach integrating functional genomic annotations for coding and noncoding variants. Nat. Genet. 48, 214-220 (2016).
(Continued)

*Primary Examiner* — Jay M. Patel
(74) *Attorney, Agent, or Firm* — Keller Preece PLLC

(57) ABSTRACT

We disclose computational models that alleviate the effects of human ascertainment biases in curated pathogenic noncoding variant databases by generating pathogenicity scores for variants occurring in the promoter regions (referred to herein as promoter single nucleotide variants (pSNVs)). We train deep learning networks (referred to herein as pathogenicity classifiers) using a semi-supervised approach to discriminate between a set of labeled benign variants and an unlabeled set of variants that were matched to remove biases.

20 Claims, 14 Drawing Sheets
(7 of 14 Drawing Sheet(s) Filed in Color)

Related U.S. Application Data

(60) Provisional application No. 62/734,116, filed on Sep. 20, 2018, provisional application No. 62/582,898, filed on Nov. 7, 2017, provisional application No. 62/573,153, filed on Oct. 16, 2017, provisional application No. 62/573,149, filed on Oct. 16, 2017, provisional application No. 62/573,144, filed on Oct. 16, 2017.

(51) Int. Cl.
*G06N 3/044* (2023.01)
*G06N 3/045* (2023.01)

(56) References Cited

U.S. PATENT DOCUMENTS

| | | | |
|---|---|---|---|
| 8,762,072 B2 | 6/2014 | Janevski et al. | |
| 10,068,557 B1 | 9/2018 | Engel et al. | |
| 10,185,803 B2 | 1/2019 | Frey et al. | |
| 10,216,895 B2 | 2/2019 | Liu | |
| 10,410,118 B2 | 9/2019 | Xiong et al. | |
| 10,423,861 B2 | 9/2019 | Gao et al. | |
| 10,540,591 B2 | 1/2020 | Gao et al. | |
| 10,558,915 B2 | 2/2020 | Gao et al. | |
| 10,770,169 B2 | 9/2020 | Vaske et al. | |
| 11,288,576 B2 | 3/2022 | Dutta et al. | |
| 11,315,016 B2 | 4/2022 | Sundaram et al. | |
| 2003/0187587 A1 | 10/2003 | Swindells et al. | |
| 2006/0228728 A1* | 10/2006 | Cox | C12Q 1/6883 435/6.16 |
| 2007/0166754 A1* | 7/2007 | Mohanlal | C12Q 1/6809 435/6.16 |
| 2011/0004110 A1* | 1/2011 | Shusterman | G16H 50/20 600/509 |
| 2011/0294681 A1* | 12/2011 | Hinds | A61P 35/00 702/19 |
| 2013/0110407 A1 | 5/2013 | Baccash et al. | |
| 2013/0203053 A1 | 8/2013 | Princen et al. | |
| 2013/0296175 A1 | 11/2013 | Rafnar et al. | |
| 2013/0332081 A1* | 12/2013 | Reese | G16B 20/00 702/19 |
| 2014/0129152 A1* | 5/2014 | Beer | G16B 20/20 702/19 |
| 2014/0304204 A1* | 10/2014 | Cameron | G16Z 99/00 706/21 |
| 2015/0324519 A1 | 11/2015 | Liu | |
| 2015/0337388 A1 | 11/2015 | Garner, Jr. et al. | |
| 2016/0004814 A1* | 1/2016 | Stamatoyannopoulos | G16B 35/00 506/8 |
| 2016/0068915 A1 | 3/2016 | Kennedy et al. | |
| 2016/0085910 A1 | 3/2016 | Bruand et al. | |
| 2016/0132637 A1* | 5/2016 | Varadan | G16B 20/00 702/19 |
| 2016/0140289 A1 | 5/2016 | Gibiansky et al. | |
| 2016/0145516 A1 | 5/2016 | Scott | |
| 2016/0196479 A1 | 7/2016 | Chertok et al. | |
| 2016/0201565 A1 | 7/2016 | Oba | |
| 2016/0275239 A1* | 9/2016 | Devogelaere | C12Q 1/6874 |
| 2016/0357903 A1 | 12/2016 | Shendure et al. | |
| 2016/0364522 A1 | 12/2016 | Frey et al. | |
| 2016/0364545 A1* | 12/2016 | Das | G16H 50/70 |
| 2016/0371431 A1 | 12/2016 | Haque et al. | |
| 2017/0169313 A1 | 6/2017 | Choi et al. | |
| 2017/0199961 A1 | 7/2017 | Yelensky et al. | |
| 2017/0286594 A1 | 10/2017 | Reid et al. | |
| 2018/0107927 A1 | 4/2018 | Frey | |
| 2018/0197067 A1 | 7/2018 | Mody et al. | |
| 2018/0322327 A1 | 11/2018 | Smith et al. | |
| 2018/0330824 A1 | 11/2018 | Athey et al. | |
| 2018/0350451 A1* | 12/2018 | Ohnemus | H04L 67/535 |
| 2019/0060428 A1 | 2/2019 | Fritsch | |
| 2019/0114511 A1 | 4/2019 | Gao et al. | |
| 2019/0114544 A1 | 4/2019 | Sundaram et al. | |
| 2019/0206521 A1* | 7/2019 | Walpole | G16H 50/30 |
| 2019/0219599 A1* | 7/2019 | O'Bryant | G16H 20/00 |
| 2019/0220704 A1 | 7/2019 | Schultz-Trieglaff et al. | |
| 2019/0232592 A1* | 8/2019 | Tran | A43B 13/187 |
| 2019/0236447 A1* | 8/2019 | Cohen | G06N 5/02 |
| 2019/0259499 A1* | 8/2019 | Hong | G16H 50/20 |
| 2019/0266491 A1 | 8/2019 | Gao et al. | |
| 2019/0266493 A1 | 8/2019 | Gao et al. | |
| 2020/0065675 A1 | 2/2020 | Sundaram et al. | |
| 2020/0098465 A1* | 3/2020 | Jiang | G16H 20/17 |
| 2020/0227137 A1* | 7/2020 | Sanborn | G16B 20/10 |
| 2020/0243167 A1* | 7/2020 | Will | G06N 20/20 |
| 2020/0279157 A1 | 9/2020 | Gao et al. | |
| 2020/0370124 A1* | 11/2020 | Hall | G16B 40/00 |
| 2020/0411199 A1* | 12/2020 | Shrager | G16H 10/20 |
| 2021/0020293 A1* | 1/2021 | Richards | G06N 3/08 |

FOREIGN PATENT DOCUMENTS

| | | |
|---|---|---|
| CN | 105378104 A | 3/2016 |
| JP | 2002505741 A | 2/2002 |
| JP | 2003527698 A | 9/2003 |
| JP | 200752774 A | 3/2007 |
| JP | 2012032163 A | 2/2012 |
| JP | 2012504761 A | 2/2012 |
| JP | 2015501974 A | 1/2015 |
| JP | 2008216557 A | 6/2017 |
| JP | 2017111830 A | 6/2017 |
| JP | 2017520821 A | 7/2017 |
| JP | 2017168866 A | 9/2017 |
| JP | 2018504784 A | 2/2018 |
| JP | 2018527647 A | 9/2018 |
| RU | 2470998 C2 | 12/2012 |
| WO | 9705552 A1 | 2/1997 |
| WO | 9854669 A1 | 12/1998 |
| WO | 2010038173 A1 | 4/2010 |
| WO | 2011139345 A2 | 11/2011 |
| WO | 2013070634 A1 | 5/2013 |
| WO | 2015173222 A1 | 11/2015 |
| WO | 2016061396 A1 | 4/2016 |
| WO | 2016145516 A1 | 9/2016 |
| WO | 2016201049 A2 | 12/2016 |
| WO | 2016201564 A1 | 12/2016 |
| WO | 2016209999 A1 | 12/2016 |
| WO | 2017172958 A1 | 10/2017 |
| WO | 2019079166 A1 | 4/2019 |
| WO | 2019079180 A1 | 4/2019 |
| WO | 2019079182 A1 | 4/2019 |
| WO | 2019136284 A1 | 7/2019 |
| WO | 2019140402 A1 | 7/2019 |

OTHER PUBLICATIONS

Kircher, M. et al. A general framework for estimating the relative pathogenicity of human genetic variants. Nat. Genet. 46, 310-315 (2014).

Shihab, H. A. et al. An integrative approach to predicting the functional effects of non-coding and coding sequence variation. Bioinformatics 31, 1536-1543 (2015).

Zhou, J., and Troyanskaya, O.G. (2015). Predicting effects of noncoding variants with deep learning-based sequence model. Nat. Methods 12, 931-934.

Lee et al., "A method to predict the impact of regulatory variants from DNA sequence." Nature genetics 47, No. 8 (2015): 21 pages.

Ritchie, Graham RS, Ian Dunham, Eleftheria Zeggini, and Paul Flicek. "Functional annotation of noncoding sequence variants." Nature methods 11, No. 3 (2014): 294.

Quang et al., "DanQ: a hybrid convolutional and recurrent deep neural network for quantifying the function of DNA sequences." Nucleic acids research 44, No. 11 (2016): e107-e107, 19 pages.

Xiong et al., "The human splicing code reveals new insights into the genetic determinants of disease." Science 347, No. 6218 (2015): 1254806, 20 pages.

Schubach et al., "Imbalance-aware machine learning for predicting rare and common disease-associated non-coding variants." Scientific reports 7, No. 1 (2017): 1-12.

(56) References Cited

OTHER PUBLICATIONS

Adzhubei, I. A. et al. A method and server for predicting damaging missense mutations. Nat. Methods 7, 248-249 (2010).
Alberts, Bruce, et al.; "How Cells Read the Genome: From DNA to Protein", Molecular Biology of The Cell, Garland Science, 6th Edition, 2015; pp. 1-3.
Alipanahi, B. et al., "Predicting the sequence specificities of DNA- and RNA-binding proteins by deep learning", Computational Biology, vol. 33(8), Aug. 2015, 9 pages.
Allen, Andrew S., et al.; "De novo mutations in the classic epileptic encephalopathies", Nature 501(7466): 217-221, 2013; pp. 1-16.
Angermueller, C. et al., "Deep learning for computational biology", Molecular Systems Biology, vol. 12, 2016, 16 pages.
Angermueller, el. al., "Accurate Prediction Of Single Cell DNA Methylation States Using Deep Learning", Apr. 11, 2017, 33 pgs.
Appenzeller, Silke, et al.; "De Novo Mutations in Synaptic Transmission Genes Including DNMI Cause Epileptic Encephalopathies", The American Journal of Human Genetics 95, 2014; pp. 360-370.
Arik, el. al., "Deep Voice: Real time Neural Text to Speech", Mar. 7, 2017, 17pgs.
Asthana, S. et al., "A limited role for balancing selection", Trends Genet., vol. 21, 2005, 30-32.
Bahar, Protein Actions Principles and Modeling, Chapter 7, 2017 pp. 165-166 (ILLM 1000-5).
Bamshad, M. et al., "Exome sequencing as a tool for Mendelian disease gene discovery", Nat. Rev. Genet., vol. 12, 2011, 745-755.
Bazykin, G. A. et al. Extensive parallelism in protein evolution. Biol. Direct 2, 20, 13 pages (2007).
Bell, C. "Comprehensive carrier testing for severe childhood recessive diseases by next generation sequencing" Sci. Transl. Med. vol. 3, 2011.
Bhande, Anup What is underfilling and overfilling in machine learning and how to deal with it, Mar. 11, 2018, 10pages (ILLM 1010-1).
Bi, Yingtao, et al. "Tree-based position weight matrix approach to model transcription factor binding site profiles", PloS One 6(9), Sep. 2, 2011, 14 pages (ILLM 1010-1).
Brandon, E. et al., "Targeting the mouse genome: a compendium of knockouts (Part II)", Curr. Biol., vol. 5 No. 7, 1995, 758-765.
Brookes, Anthony J., "The essence of SNPs", 1999, pp. 177-186 (ILLM 1000-5).
Caron , et al., "NCBoost classifies pathogenic non-coding variants in Mendelian diseases through supervised earning on purifying selection signals in humans", Genome Biology, Feb. 11, 2019, 22 pages.
Carter et al., "Cancer-specific high-throughput annotation of somatic mutations: computational prediction of driver missense mutations," Cancer research 69, No. 16 (2009): pp. 6660-6667 (ILLM 1010-2).
Carter, H. et al., "Identifying Mendelian disease genes with the variant effect scoring tool", BMC Genom, vol. 14, 2013, 16 pages.
Chang, Chia-Yun, et al. "Oversampling to overcome overfilling: exploring the relationship between data set composition, molecular descriptors, and predictive modeling methods", Journal of chemical information and modeling, 53, Mar. 6, 2013, pp. 958-971, (ILLM 1010-1).
Chen, Hua; "A Computational Approach for Modeling the Allele Frequency Spectrum of Populations with Arbitrarily Varying Size", Genomics Proteomics and Bioinformatics, 2019, vol. 17, No. 6; pp. 635-644.
Chen LC et al., Deeplab: Semantic image segmentation with deep convolutional nets, Atrous convolution, and fully connected crfs. IEEE transactions on pattern analysis and machine intelligence. Apr. 27, 2017,40(4):834-48. (Year: 2017).
Chen, Kathleen M., et al., "Selene: a PyTorch based deep learning library for sequence level data", Oct. 10, 2018, 15pages.
Chimpanzee Sequencing Analysis Consortium. Initial sequence of the chimpanzee genome and comparison with the human genome. Nature 437, 69-87 (2005).
Ching, el. al., "Opportunities and Obstacles for Deep Learning in Biology and Medicine", May 26, 2017, 47pgs.

Ching, T. et al., "Opportunities and obstacles for deep learning in biology and medicine", https://doi.org/10.1101/142760 ., Jan. 19, 2018, 123 pages.
Choi, Yongwook, et al.; "Predicting the Functional Effect of Amino Acid Substitutions and Indels", Plos One, Oct. 2012, vol. 7, Issue 10; pp. 1-13.
Chun, S. et al., "Identification of deleterious mutations within three human genomes", Genome Res., vol. 19, 1553-1561, 2009.
Davydov, E. V. et al. Identifying a high fraction of the human genome to be under selective constraint using GERP++. PloS Comput. Biol. 6, Dec. 2, 2010, 13 pages.
dbSNP rs2241788 [Retrieved on Mar. 13, 2019], Retrieved from the Internet<https://www.ncbi.nlm.nih.gov/snp/rs2241788>, 5 pages (ILLM 1000-8WO).
De Ligt, J. et al., "Diagnostic exome sequencing in persons with severe intellectual disability", N. Engl. J. Med, vol. 367, 2012, 1921-1929.
De Manuel, M. et al., "Chimpanzee genomic diversity reveals ancient admixture with bonobos", Science, vol. 354, 2016, 477-481.
De Rubeis, S. et al., "Synaptic, transcriptional and chromatin genes disrupted in autism", Nature, vol. 515, 2014, 209-215.
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Despois, Julien, "Memorizing is not learning!—6 tricks to prevent overfilling in machine learning", Mar. 20, 2018, 17 pages (ILLM 1010-1).
Dong, C. et al., "Comparison and integration of deleteriousness prediction methods for nonsynonymous SNVs in whole exome sequencing studies", Hum. Mal. Genet., vol. 24, 2015, 2125-2137.
Douville et al., Assessing the Pathogenicity of Insertion and Deletion Variants with the Variant Effect Scoring Tool, Human mutation, dated 2016, vol. 37, No. 1, pp. 28-35. (ILLM 1000-8RU).
Duggirala, Ravindranath, et. al.,"Genome Mapping and Genomics in Human and Non Human Primate", 2015, 306pgs (ILLM 1000-5).
Dunbrack, Roland L., Re: Question about your Paper titled "The Role of Balanced Training and Testing Data Sets for Binary Classifiers in Bioinformatics", Message to Sikander Mohammed Khan, Feb. 3, 2019, E-mail, 3pgs (ILLM 1000-8).
Eigen, Columbia University 2015, http://www.columbia.edu/~ii2135/information_eigen.html, accessed Dec. 19, 2018, 1 page.
Estrada, A. et al. Impending extinction crisis of the world's primates: why primates matter. Sci. Adv. 3, e1600946 (2017), 17 pages.
Famiglietti, M. L. et al. Genetic variations and diseases in UniProtKB/Swiss-Prot: the ins and outs of expert manual curation. Human. Mutat. 35, 927-935 (2014).
Flygare, Steven, et al.; "The VAAST Variant Prioritizer (WP): ultrafast, easy to use whole genome variant prioritization tool", BMC Bioinformatics, 2018, 19:57; pp. 1-13.
Fu H, Yang L, Zhang X. Noncoding variants functional prioritization methods based on predicted regulatory factor binding sites. Current genomics. Aug. 1, 2017;18(4):322-31. (Year: 2017).
Gao, Tingting, et al. "Identifying translation initiation sites in prokaryotes using support vector machine," Journal of Theoretical biology, 262, Oct. 17, 2010, 644-649 (ILLM 1010-1).
Geeks for Geeks, "Underfilling and Overfilling in Machine Learning", [retrieved on Aug. 26, 2019]. Retrieved from the Internet <https://www.geeksforgeeks.org/underfitting-and-overfitting-in-machine-learning/>, 2 pages (ILLM 1010-1).
Genomes Project Consortium, et al., "A global reference for human genetic variation", Nature 526, 2015, 68-74.
Gilissen, C. et al., "Genome sequencing identifies major causes of severe intellectual disability", Nature, vol. 511, 2014, 344-347.
Goodfellow, et al., "Convolutional Networks", http://www.deeplearningbook.org/contents/convnets.html, Oct. 14, 2017, 41 pages.
Grantham, R. "Amino acid difference formula to help explain protein evolution", Science, vol. 185, 1974, 862-864.

(56) References Cited

OTHER PUBLICATIONS

Grimm, D. G. The evaluation of tools used to predict the impact of missense variants is hindered by two types of circularity. Human. Mutat. 36, 513-523 (2015).
Grob, C. et al., "Predicting variant deleteriousness in non-human species Applying the CADD approach in mouse", 2018, 1-11.
Gu, J. et al., "Recent Advances in Convolutional Neural Networks", Nanyang Technological University, Singapore, Jan. 5, 2017, 37 pages.
Gulko, B. et al., "A method for calculating probabilities of fitness consequences for point mutations across the human genome", Nat Genet., vol. 47, 2015, 276-283.
Harpak, A., Bhaskar, A., & Pritchard, J. K. Mutation rate variation is a primary determinant of the distribution of allele frequencies in humans. PLoS Genet. Dec. 15, 2016, 22pgs.
He, K. et al., "Identity mappings in deep residual networks. in 14th European Conference on Computer Vision—ECCV 2016", Lecture Notes in Computer Science, vol. 9908, 2016, 630-645.
He, Kaiming, et. al., "Deep Residual Learning for Image Recognition", Dec. 10, 2015, 12 pages. (ILLM 1000-5).
Heffernan, R. et al. Improving prediction of secondary structure, local backbone angles, and solvent accessible surface area of proteins by iterative deep learning. Sci. Rep. 5, 11476 (2015) 11 pages.
Henikoff, et al., "Amino Acid Substitution Matrices from Protein Blocks", PNAS, 89, 1992, 10915-10919.
Horaitis, O., Talbot, C. C. Jr., Phommarinh, M., Phillips, K. M., & Cotton, R. G. A database of locus-specific databases. Nat. Genet. 39, 425 (2007).
Huang, G. et al., "Densely Connected Convolutional Networks", Aug. 27, 2017, 9 pages.
Ioannidis, N. et al., "REVEL: an ensemble method for predicting the pathogenicity of rare missense variants", Am. J. Hum. Genet., vol. 99, 2016, 877-885.
Ioffe, S. et al., "Batch Normalization: Accelerating Deep Network Training by Reducing Internal Covariate Shift", arXiv:1502.03167 [cs.LG], Mar. 2, 2015, 11 pages.
Ionita-Laza, Iuliana, et al.; Eigen homepage, Columbia University 2015; p. 1.
Iossifov, I. et al., "De nova gene disruptions in children on the autistic spectrum", Neuron, vol. 74, 2012, 285-299.
Iossifov, I. et al., "The contribution of de novo coding mutations to autism spectrum disorder", Nature, vol. 515, 2014, 216-221.
Jagadeesh, K. et al., "M-CAP eliminates a majority of variants of uncertain significance in clinical exomes at high sensitivity", Nat. Genet., vol. 48, 2016, 1581-1586.
Jain, S. et al., "Recovering true classifier performance in positive-unlabeled learning", Thirty-First AAAI Conference on Artificial Intelligence, 2017, 2066-2072.
Joosten, R. P. et al. A series of PDB related databases for everyday needs. Nucleic Acids Res. 39, 411-419 (2011).
Kabsch, W. et al., "Dictionary of protein secondary structure: pattern recognition of hydrogen-bonded and geometrical features", Biopolymers, vol. 22, 1983, 2577-2637.
Karczewski et al., "The Genome Aggregation Database (gnomAD)." MacArthur Lab (2017), 19 pages.
Karczewski, Konrad J., et al.; "The mutational constraint spectrum quantified from variation in 141,456 humans", Nature, MacMillan Journals Ltd., etc., London, vol. 581, No. 7809; pp. 1-24.
Karydis, Thrasyvoulos. "Learning hierarchical motif embeddings for protein engineering." PhD diss., Massachusetts Institute of Technology, Feb. 2017, 78 pages.
Kent, W. et al., "The human genome browser at UCSC", Genome Res., vol. 12, 2002, 996-1006.
Klein, S. et al., "The molecular descent of the major histocompatibility complex", Annu. Rev Immunol, vol. 11, 1993, 269-295.
Korhonen, Janne H., et al., "Fast motif matching revisited: high-order PWMs, SNPs and indels", Bioinformatics, 33 (4), Dec. 5, 2016, pp. 514-521 (ILLM 1010-1).
Krizhevsky, Alex, et al, ImageNet Classification with Deep Convolutional Neural Networks, 2012, 9 Pages (ILLM 1010-1).
Lanchantin J, Sekhon A, Singh R, Qi Y. Prototype Matching Networks for Large-Scale Multi-label Genomic Sequence Classification. arXiv preprint arXiv: 1710 .11238. Oct. 30, 2017.: (Year: 2017).
Landrum, M. et al., "ClinVar: public archive of interpretations of clinically relevant variants", Nucleic Acids Res., vol. 44, 2016, 862-868.
Lecun, Y. et al., "Gradient based learning applied to document recognition", Proc. IEEE, vol. 86, 1998, 2278-2324.
Leffler, E. et al., "Multiple instances of ancient balancing selection shared between humans and chimpanzees", Science, vol. 339, 2013, 1578-1582.
Leffler, E. M. et al. Revisiting an old riddle: what determines genetic diversity levels within species? PLoS Biol. 10, e1001388 (2012), 9pages.
Lek, M. et al., "Analysis of protein-coding genetic variation in 60,706 humans", Genet. Med. Nature, vol. 536, 2016, 285-291.
Lelieveld, S. et al., "Meta-analysis of 2,104 trios provides support for 10 new genes for intellectual disability", Nat. Neurosci, vol. 19, 2016, 1194-1196.
Leung, M. et al., "Deep Learning of the tissue-regulated splicing code", Bioinformatics, vol. 30, Jul. 23, 2014, 121-129.
Leung, M. et al., "Inference of the Human Polyadenylation Code", bioRxiv, 2017, 13 pages.
Leung, M. et al., "Machine Learning in Genomic Medicine: A Review of Computational Problems and Data Sets", IEEE, vol. 104, No. 1, Jan. 2016, 176-197.
Li, B. et al., "Automated inference of molecular mechanisms of disease from amino acid substitutions", Bioinformatics, vol. 25, 2009, 2744-2750.
Li, et al., "FoldingZero: Protein Folding from Scratch in Hydrophobic Polar Model", Dec. 3, 2018, 10 pages.
Li, Gangmin, et al., "Classification of Genetic Mutations for Cancer Treatment with Machine Learning Approaches" International Journal of Design, Analysis and Tools for Integrated Circuits and Systems, vol. 7, No. 1, Oct. 1, 2018, pp. 63-66, (ILLM 1010-1).
Li, W. et al., "Nonrandomness of point mutation as reflected in nucleotide substitutions in pseudogenes and its evolutionary implications", J. Malec. Evol., vol. 21, 1984, 58-71.
Libbrecht, M. et al., "Machine learning in genetics and genomics", Nat Rev Genet., vol. 16(6), Jun. 2015, 321-332.
Lieschke, J. et al., "Animal models of human disease: zebrafish swim into view", Nat. Rev. Genet., vol. 8, 2007, 353-367.
Lin et al., Computational identification and characterization of primate-specific microRNAs in human genome, computational Biology and Chemistry, Aug. 24, 2010, vol. 34, Issue.4, pp. 232-241.
Liu, X. et al., "dbNSFP: A lightweight database of human nonsynonymous SNPs and their functional predictions", Human Mutat., vol. 32, 2011, 894-899.
Liu, X. et al., "dbNSFPv3.0: a one-stop database of functional predictions and annotations for human nonsynonymous and splice-site SNVs", Human Mutat, vol. 37, 2016, 235-241.
Locke, D. et al., "Comparative and demographic analysis of orang-utan genomes", Nature, vol. 469, 2011, 529-533.
Lu, Q. et al. A statistical framework to predict functional non-coding regions in the human genome through integrated analysis of annotation data. Sci. Rep. 5, 10576 (2015), 13pgs.
MacArthur, D. G. et al. Guidelines for investigating causality of sequence variants in human disease. Nature 508, 469-476 (2014).
Mallick, S. et al., "The Simons Genome Diversity Project: 300 genomes from 142 diverse populations", Nature, vol. 538, 2016, 201-206.
Martin-Navarro, Antonio, et al., "Machine learning classifier for identification of damaging missense mutations exclusive to human mitochondrial DNA-encoded polypeptides", BMC bioinformatic, 18:158, (2017), 12 pages (ILLM 1010-1).
Min, S. et al., "Deep Learning in Bioinformatics", Dept. of Electrical and Computer Engineering, Seoul National University, Jul. 25, 2016, 46 pages.
Nakamura, K. et al., "Clinical spectrum of SCN2A mutations expanding to Ohtahara syndrome", Neurology, vol. 81, 2013, 992-998.

(56) References Cited

OTHER PUBLICATIONS

Neale, B. et al., "Patterns and rates of exonic de novo mutations in autism spectrum disorders", Nature, vol. 485, 2012, 242-245.
Ng, P. et al., "Predicting deleterious amino acid substitutions", Genome Res., vol. 11, 2001, 863-874.
O'Roak, B. et al., "Sporadic autism exomes reveal a highly interconnected protein network of de nova mutations", Nature, vol. 485, 2012, 246-250.
Ohta, T. et al., "Slightly deleterious mutant substitutions in evolution", Nature, vol. 246, 1973, 96-98.
Park, el. al., "Deep Learning for Regulatory Genomics", Aug. 2015, 2pgs.
Payandeh, J. et al., "The crystal structure of a voltage-gated sodium channel", Nature, vol. 475, 2011, 353-358.
Piqueras, L. "Autogressive Model Based on a Deep Convolutional Neural Network for Audio Generation", Master of Science Thesis, Dec. 7, 2016, 58 pages.
Prado-Martinez, J. et al., "Great ape genome diversity and population history", Nature, vol. 499, 2013, 471-475.
Prakash et al., "A survey on semi-supervised learning techniques." arXiv preprint arXiv:1402.4645, 8 pages (2014).
Quang, D. et al., "DANN: a deep learning approach for annotating the pathogenicity of genetic variants", Bioinformatics, vol. 31, 2015, 761-763.
Rauch, A. et al., "Range of genetic mutations associated with severe non-syndromic sporadic intellectual disability: an exome sequencing study", Lancet, vol. 380, 2012, 1674-1682.
Reed, el. al., "Training Deep Neural Networks on Noisy Labels with Bootstrapping", 2015, 11 pages (ILLM 1000-10).
Rehm, H. "Evolving health care through personal genomics", Nat. Rev. Genet., vol. 18, 2017, 259-267.
Rehm, H. et al., "ClinGen—the Clinical Genome Resource", N. Engl. J. Med., vol. 372, 2015, 2235-2242.
Reich, D. et al., "On the allelic spectrum of human disease", Trends Genet., vol. 17, 2001, 502-510.
Rentzsch, P. et al., "CADD: predicting the deleterious of variants throughout the human genome", Nucleic Acids Research (1), Sep. 14, 2018, 1-9.
Reva, B., Antipin, Y., & Sander, C. Predicting the functional impact of protein mutations: application to cancer genomics. Nucleic Acids Res. 39, e118 (2011), 14pgs.
Rhesus Macaque Genome Sequencing Analysis Consortium. Evolutionary and biomedical insights from the rhesus macaque genome. Science 316, 222-234 (2007).
Richards, S. et al., "Standards and guidelines for the interpretation of sequence variants: a joint consensus recommendation of the American College of Medical Genetics and Genomics and the Association for Molecular Pathology", Genet. Med., vol. 17, 2015, 405-424.
Samocha, K. E. et al. A framework for the interpretation of de novo mutation in human disease. Nat. Genet. 46, 944-950 (2014).
Sanders, S. et al., "De novo mutations revealed by whole-exome sequencing are strongly associated with autism", Nature, vol. 485, 2012, 237-241.
Schrago, C. et al., "Timing the origin of New World monkeys", Mal. Biol., vol. 20, 2003, 1620-1625.
Schwarz, J. et al., "MutationTaster evaluates disease-causing potential of sequence alterations", Nat. Methods, vol. 7, 2010, 575-576.
Shen, H. et al. Structure of a eukaryotic voltage-gated sodium channel at near-atomic resolution. Science 355, eaal4326 (2017), 19 pages.
Sherry, S. T. et al. dbSNP: the NCBI database of genetic variation. Nucleic Acids Res. 29, 308-311 (2001).
Shihab, H. et al., "Predicting the functional, molecular, and phenotypic consequences of amino acid substitutions using hidden Markov models", Human Mutat., vol. 34, 2013, 57-65.
Sittig, L. et al., "Genetic background limits generalizability of genotype-phenotype relationships", Neuron, vol. 91, 2016, 1253-1259.
Smedley, D. et al., "A whole-genome analysis framework for effective identification of pathogenic regulatory variants in mendelian disease", Am. J. Hum., vol. 99, 2016, 595-606.
Srivastava, R. et al., "Highway Networks", The Swiss AI Lab, Nov. 3, 2015, 6 pages.
Stanescu et. al., "An empirical study of ensemble-based semi-supervised learning approaches for imbalanced splice site datasets", BMC Systems Biology, dated Sep. 1, 2015, vol. 9, Article S1, pp. 1-12 (ILLM.1000-10 JP).
Stanescu, et al., "Ensemble-based semi-supervised learning approaches for imbalanced splice site datasets," In 2014 EEE International Conference on Bioinformatics and Biomedicine (BIBM), pp. 432-437. IEEE, 2014.
Stenson, P. et al., "The Human Gene Mutation Database: building a comprehensive mutation repository for clinical and molecular genetics, diagnostic testing and personalized genomic medicine", Hum. Genet., vol. 133, 2014, 1-9.
Sundaram L. et al., "Predicting the clinical impact of human mutation with deep neural networks," Nature genetics 50, No. 8 (2018): pp. 1161-1173.
Szegedy, C. et al., "Going deeper with convolutions", Sep. 17, 2014, 12 pages.
Takahata, N. "Allelic genealogy and human evolution", Mal. Biol. Evol., vol. 10, 1993, 2-22.
Torng, W. et al., "3D deep convolutional neural networks for amino acid environment similarity analysis", BMC Bioinformatics 18(302), 2017, 1-23.
Tyner, C. et al. The UCSC Genome Browser database: 2017 update. Nucleic Acids Res. 45, D626-D634 (2017).
UniProtKB P04217 A1BG Human [retrieved on Mar. 13, 2019]. Retrieved from the Internet <hllps://www.uniprol.org/uniprol/P04217>, 12pages.
Van Den Oord, A. "WaveNet: A generative Model for raw audio", Sep. 19, 2016, 15 pages.
Van Der Velde, et al., "GAVIN: Gene-Aware Variant INterpretation for medical sequencing", Genome Biology, Jan. 16, 2017, 10 pages.
Vikram et al., "SSCM: A method to analyze and predict the pathogenicity of sequence variants." bioRxiv (2015): 021527, 30 pages.
Vissers, L. et al., "Genetic studies in intellectual disability and related disorders", Nat. Rev. Genet., vol. 17, 2016, 9-18.
Wang D, Lee NK. MISCORE: Mismatch-based matrix similarity scores for DNA motif detection. In International Conference on Neural Information Processing Nov. 25, 2008 (pp. 478-485). Springer, Berlin, Heidelberg. (Year: 2008).
Wang, S., Peng, J., Ma, J. & Xu, J. Protein secondary structure prediction using deep convolutional neural fields. Sci. Rep. 6, 18962-18962 (2016).
Wei et al. The Role of Balanced Training and Testing Data Sets for Binary Classifiers in Bioinformatics dated Jul. 9, 2013 12 pages (Illm 1000-8WO).
Wei, el. al., "Prediction of phenotypes of missense mutations in human proteins from biological assemblies", Feb. 2013, 28 pages. (ILLM 1000-5).
Whiffin, N. et al., "Using high-resolution variant frequencies to empower clinical genome interpretation", Genet. Med., vol. 19, 2017, 1151-1158.
Wolterink, J. et al., "Dilated Convolutional Neural Networks for Cardiovascular MR Segmentation in Congenital Heart Disease", Apr. 21, 2017, 9 pages.
Wong, Sebastien C., et al., "Understanding data augmentation for classification: when to warp?", International Conference on Digital Image Computing: Techniques and Applications (DICTA). IEEE, 2016, 6 pages (ILLM 1010-1).
Worley, K. et al., "The common marmoset genome provides insight into primate biology and evolution", Nat. Genet., vol. 46, 2014, 850-857.
Wu, J. "Introduction to Convolutional Neural Networks", National Key Lab for Novel Software Technology, May 1, 2017, 16 pages.
Yu, F. et al., "Multi-scale context aggregation by dilated convolutions", Apr. 30, 2016, 13 pages.
Yue, T. et al., "Deep Learning for Genomics: A Concise Overview", School of Computer Science, May 8, 2018, 40 pages.

(56) References Cited

OTHER PUBLICATIONS

Yuen, R. et al., "Genome-wide characteristics of de nova mutations in autism", Genomic Medicine, Jun. 13, 2016, 10 pages.

Zhang et al., "Discerning novel splice junctions derived from RNA-seq alignment: A deep learning approach." BMC genomics 19, No. 1 (2018): 971.

Zhang, Jun, el. al. "PSFM-DBT: identifying DNA-binding proteins by combing position specific frequency matrix and distance -bi gram transformation", International journal of molecular sciences, 18, Jul. 29, 2017, 16 pages (ILLM 1010-1).

Zhu, X. et al., "One gene, many neuropsychiatric disorders: lessons from Mendelian diseases", Nat. Neurosci., vol. 17, 2014, 773-781.

Zou, J. et al., "A primer on deep learning in genomics", Nature Genetics, Nov. 26, 2018, 1-7.

* cited by examiner

Residual Block (RB) (N, W, D)

N: Number of Convolution Filters
W: Convolution Window Size
D: Atrous Convolution Rate

|   | A | ... | T | G | C | ... | ? | ... | T | ... |
|---|---|---|---|---|---|---|---|---|---|---|
| A | 1 | 0 | 0 | 0 | 0 | 0 | 1 | 0 | 1 | 0 |
| C | 0 | 1 | 0 | 0 | 0 | 1 | 0 | 1 | 0 | 0 |
| G | 0 | 0 | 1 | 0 | 1 | 0 | 1 | 0 | 0 | 0 |
| T | 0 | 0 | 0 | 1 | 1 | 1 | 0 | 0 | 0 | 1 | 0 |
| N | 0 | 0 | 0 | 0 | 0 | 0 | 0 | 0 | 0 | 0 |

Reference Bases in Input Promoter Sequences

↑ One-hot Encoding

DEEP LEARNING-BASED PATHOGENICITY CLASSIFIER FOR PROMOTER SINGLE NUCLEOTIDE VARIANTS (PSNVS)

PRIORITY APPLICATIONS

This application claims priority to or the benefit of U.S. Provisional Patent Application No. 62/734,116, titled, "Deep Learning-Based Pathogenicity Classifier for Promoter Single Nucleotide Variants (pSNVs)," filed Sep. 20, 2018. The provisional application is hereby incorporated by reference for all purposes.

This application is a continuation-in-part of U.S. patent application Ser. No. 16/160,903, titled, "Deep Learning-Based Techniques for Training Deep Convolutional Neural Networks," filed Oct. 15, 2018, which claims priority to or the benefit of U.S. Provisional Patent Application No. 62/573,144, titled, "Training a Deep Pathogenicity Classifier Using Large-Scale Benign Training Data," filed Oct. 16, 2017; U.S. Provisional Patent Application No. 62/573,149, titled, "Pathogenicity Classifier Based On Deep Convolutional Neural Networks (CNNS)," filed Oct. 16, 2017; U.S. Provisional Patent Application No. 62/573,153, titled, "Deep Semi-Supervised Learning that Generates Large-Scale Pathogenic Training Data," filed Oct. 16, 2017; and U.S. Provisional Patent Application No. 62/582,898, titled, "Pathogenicity Classification of Genomic Data Using Deep Convolutional Neural Networks (CNNs)," filed Nov. 7, 2017. The non-provisional and provisional applications are hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genetic variations can help explain many diseases. Every human being has a unique genetic code and there are lots of genetic variants within a group of individuals. Most of the deleterious genetic variants have been depleted from genomes by natural selection. It is important to identify which genetics variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of non-coding variants remains a great challenge due to the complexity of cell type-specific transcription regulation systems. In addition, a limited number of non-coding variants have been functionally validated by experiments.

Previous efforts on interpreting genomic variants have mainly concentrated on variants in the coding regions. However, the non-coding variants also play an important role in complex diseases. Identifying the pathogenic functional non-coding variants from the massive neutral ones can be important in genotype-phenotype relationship research and precision medicine.

Furthermore, most of the known pathogenic non-coding variants reside in the promoter regions or conserved sites, causing ascertainment bias in the training set because easy or obvious cases known for pathogenic tendencies are likely to be enriched in labeled data sets relative to the entire population of the pathogenic non-coding variants. If left unaddressed, this bias in the labeled pathogenic data would lead to unrealistic model performance, as a model could achieve relatively high test set performance simply by predicting that all core variants are pathogenic and all others are benign. However, in the clinic, such a model would incorrectly classify pathogenic, non-core variants as benign at an unacceptably high rate.

Advances in biochemical technologies over the past decades have given rise to next generation sequencing (NGS) platforms that quickly produce genomic data at much lower costs than ever before. Such overwhelmingly large volumes of sequenced DNA remain difficult to annotate. Supervised machine learning algorithms typically perform well when large amounts of labeled data are available. In bioinformatics and many other data-rich disciplines, the process of labeling instances is costly; however, unlabeled instances are inexpensive and readily available. For a scenario in which the amount of labeled data is relatively small and the amount of unlabeled data is substantially larger, semi-supervised learning represents a cost-effective alternative to manual labeling.

An opportunity arises to use semi-supervised algorithms to construct deep learning-based pathogenicity classifiers that accurately predict pathogenicity of non-coding variants. Databases of pathogenic non-coding variants that are free from human ascertainment bias may result.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 12 shows the one-hot encoding scheme used to encode reference bases in the input promoter sequences.

DETAILED DESCRIPTION

Figure 1:
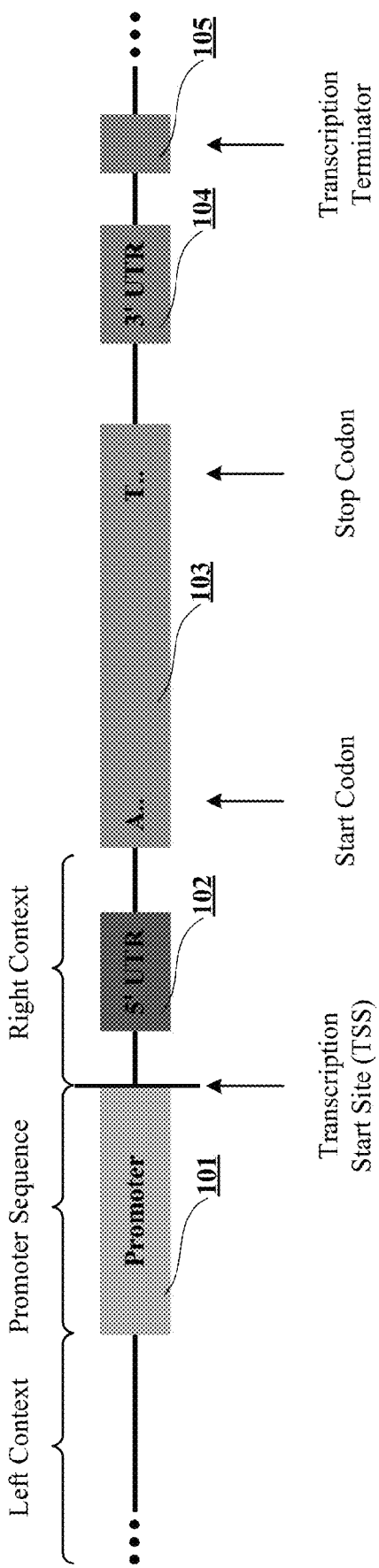
FIG. 1 shows an example promoter sequence of a gene. The disclosed ensemble of pathogenicity classifiers predicts pathogenicity scores for promoter single nucleotide variants (pSNVs) located in multitude of promoter sequences.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

Disclosed are computational models that alleviate the effects of human ascertainment biases in curated pathogenic non-coding variant databases by generating pathogenicity scores for variants occurring in the promoter regions (referred to herein as promoter single nucleotide variants (pSNVs)).

The numbers that follow are given relative to a promoter sequence of length 3001 bases. These numbers can vary in alternative implementations. As the length of the promoter sequence changes, so will the number of possible combinations.

First, a benign training dataset of largely common benign pSNVs from human and non-human primates can be constructed based on the observation that common variants in other primate species are largely clinically benign in human. At the time of this application, 8,048,977 pSNVs were observed and labeled as benign.

To obtain an unlabeled training dataset that complements the benign training dataset, all possible variants from each unobserved base position in the promoter regions are generated by substituting the base at the position with the other three bases. At the time of this application, 108,000,000 unlabeled pSNVs were generated. Variants located in homopolymer regions, low-complexity regions, and overlapping coding regions are excluded.

In some implementations, deep learning networks (referred to herein as pathogenicity classifiers) are trained using a semi-supervised approach to discriminate between a set of labeled benign variants and an unlabeled set of variants that were matched to remove biases.

The unlabeled training dataset is likely to be a mixture of benign and pathogenic pSNVs. By treating the substitutionally generated variants as unlabeled data, the pathogenicity classifiers learn the distributions of benign and pathogenic variants without needing an explicit pathogenic training set.

In some implementations, a set of unlabeled variants is sampled with replacement, requiring weighted sampling with the benign variants that takes into account trinucleotide context distribution and local GC-content distribution (to control for mutational rate, genetic drift, and gene conversion), and sequence coverage distribution (to adjust for the impact of alignability and sequence coverage on variant ascertainment). Balanced sampling of unlabeled variants helps remove biases that are unrelated to the pathogenicity of the variant. In absence of proper control of confounding effects, deep learning networks can easily pick up on inadvertently introduced biases to discriminate between the classes.

Because the number of unlabeled variants greatly exceeds the labeled benign variants, a consensus prediction can be obtained by training an ensemble of the deep learning networks that use the same set of labeled benign variants and separately sampled sets of unlabeled variants. The consensus is formed by taking the average of their predictions on inference data comprising all observed and unobserved pSNVs. The ensemble can have 10, 100, or 200 deep learning networks. The deep learning networks can be convolutional neural networks or recurrent neural networks, or a combination of the two. Sets of variants are randomly sampled for validation and testing, which can be withheld from training.

Numerous training examples are produced to train the deep learning networks. Each training example corresponds to an input promoter sequence that contains reference bases at observed positions, unobserved-sampled positions, and unobserved-unsampled positions.

The input is supplemented with output scores of protein binding affinity and DNA accessibility inducing networks. Although predictions of protein binding or DNA accessibility do not directly translate to pathogenicity predictions, models trained to predict binding or DNA accessibility can discover informative patterns of the DNA sequence. Such patterns can therefore be used to pre-train pathogenicity classifiers, thus further improving the ability of our models to learn from unlabeled data.

Each training example is annotated with sparsely encoded ground truth data with base-wise and position-wise labels for each input promoter sequence, including blank, benign, or pathogenic labels to identify variations from the reference bases.

From the training, trained pathogenicity classifiers can be derived, which, in a single invocation during inference, produce pathogenicity scores for each of the three base variations from the reference bases. So, if the input promoter sequence contains 3000 reference bases, then the inference output of a trained pathogenicity classifier includes pathogenicity scores for up to 9000 base variations. More details follow.

Training Data

FIG. 1 shows an example promoter sequence 101 of a gene. The disclosed ensemble of pathogenicity classifiers predicts pathogenicity scores for promoter single nucleotide variants (pSNVs) located in multitude of promoter sequences. The input to the pathogenicity classifiers are promoter sequences, which are regulatory regions located upstream (towards the 5' region) of the gene, adjacent to the transcription start site (TSS). They do not code for proteins and instead provide an initiation and control point for regulated gene transcription.

In one implementation, the length of the promoter sequences is 3001 bases. In other implementations, the length can be decreased or increased, for instance from 200 to 20,000 bases, or it can be adapted to specific promoter regions (e.g., be centered at the TSS). The promoter sequences are flanked by right and left context that extends outside the promoter region, including into the gene sequence that follows the promoter region (e.g., 5' UTR regions 102, start and stop codons 103, 3' UTR regions 104, transcription terminator 105). The flanking context can be 100 to 5000 bases. Typically, the upstream and downstream flanking contexts are equal, but that is not essential.

Figure 11:
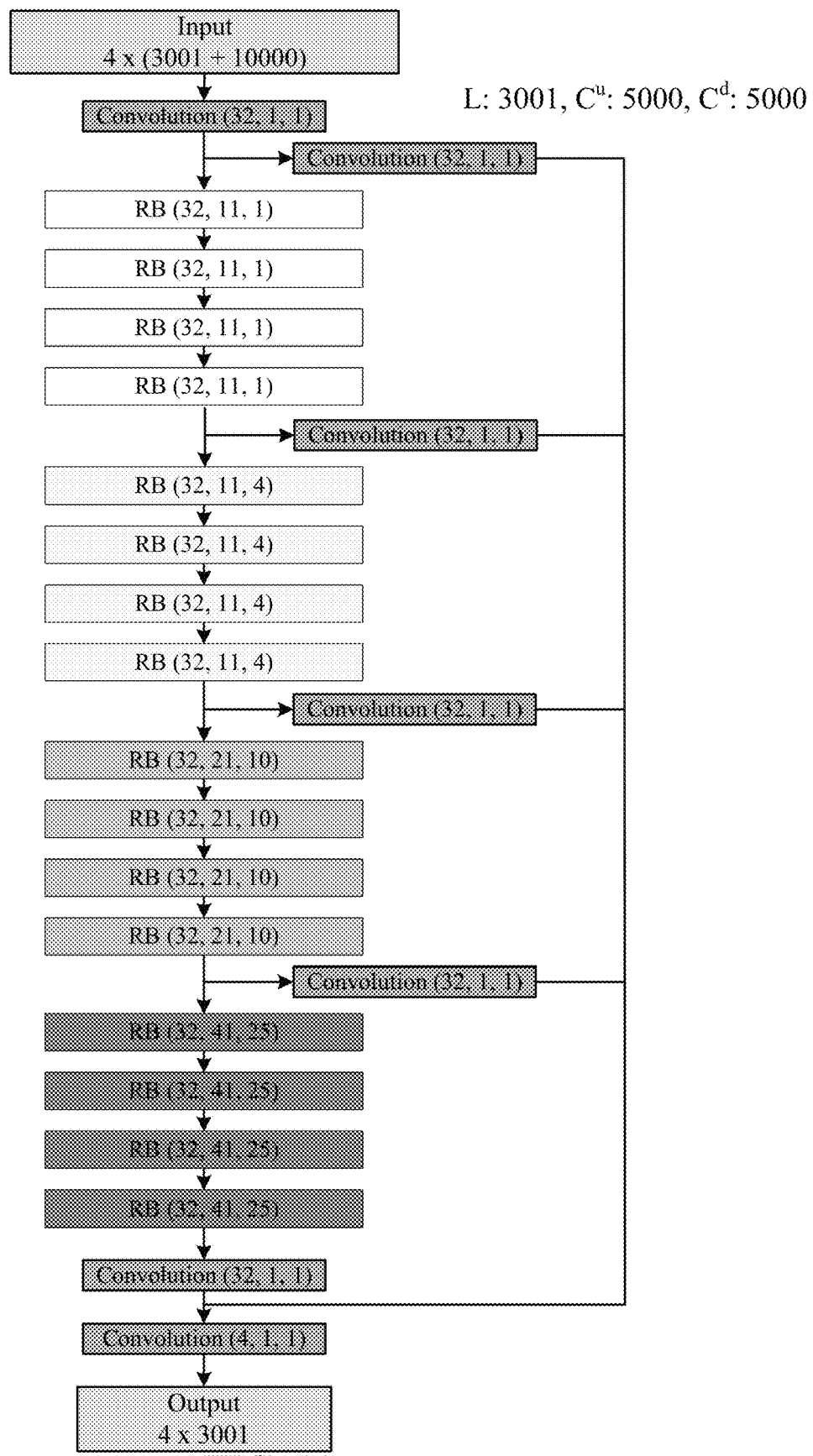
FIG. 11 is yet another example deep convolutional neural network-based architecture used to construct the pathogenicity classifiers.

The promoter sequences contain reference bases from one or more reference genome databases. The reference bases are one-hot encoded to conserve the position-specific information of each individual base in the promoter sequences. In one-hot encoding, each reference base is encoded with a binary vector of four bits, with one of the bits being hot (i.e., 1) while others being off (i.e., 0). For instance, T=(1, 0, 0, 0), G=(0, 1, 0, 0), C=(0, 0, 1, 0), and A=(0, 0, 0, 1). In some implementations, an undetermined base is encoded as N=(0, 0, 0, 0). FIG. 11 shows an example promoter sequence (in yellow) with reference bases represented using one-hot encoding. When the pathogenicity classifiers, as convolutional neural networks, receive the one-hot encoded reference bases, they are able to preserve the spatial locality relationships within the promoter sequences.

Figure 2:
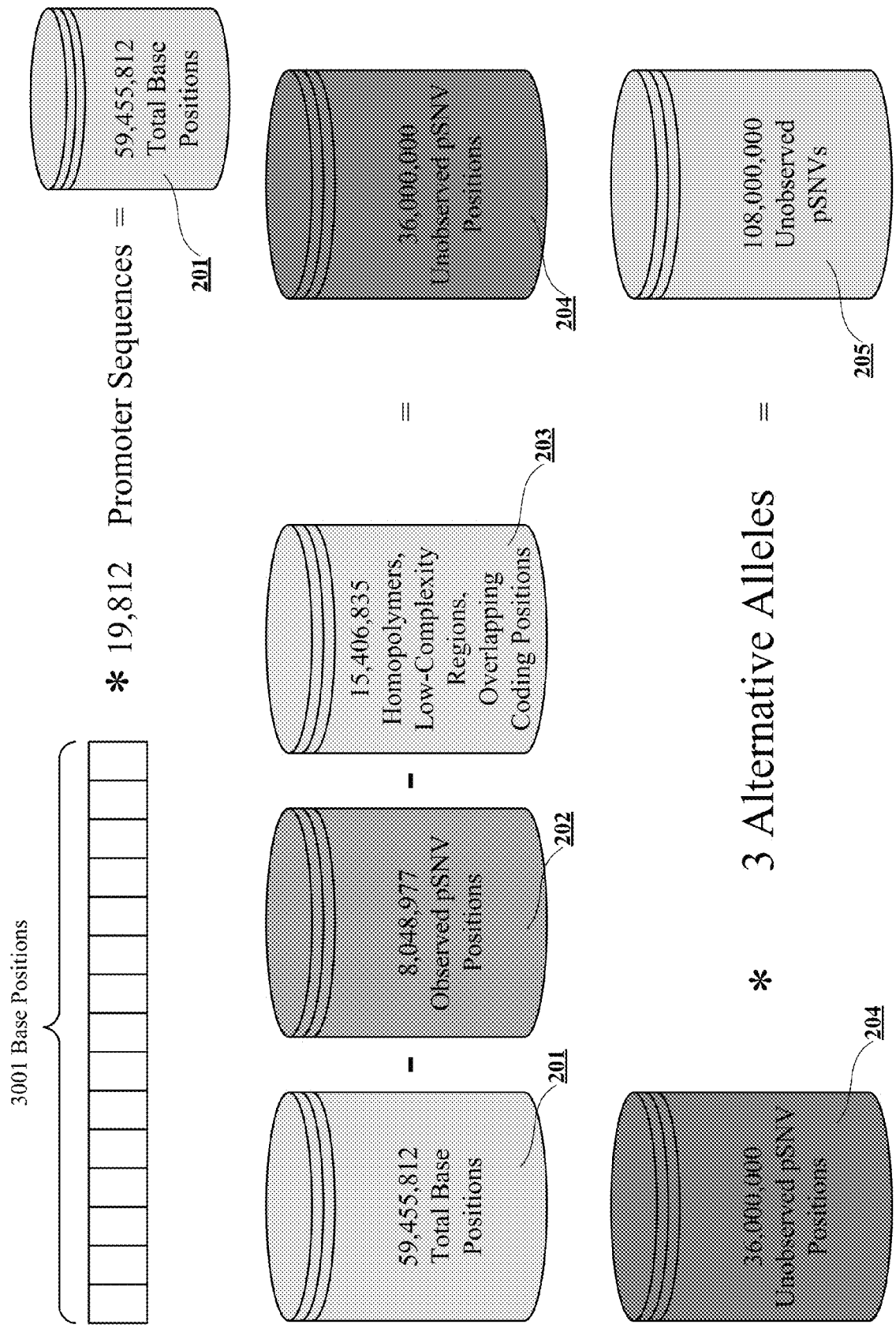
FIG. 2 depicts how training datasets used for training the pathogenicity classifiers are generated.

FIG. 2 depicts how training datasets used for training the pathogenicity classifiers are generated. First, promoter sequences in 19,812 genes are identified, according to one implementation. In some implementations, each of the 19,812 promoter sequences has 3001 base positions (not including the flanking contexts outside the promoter region), which produces 59,455,812 total base positions 201 (in grey).

In one implementation, from the 59,455,812 total base positions 201, 8,048,977 observed pSNV positions 202 are qualified as benign positions. 8,048,977 benign positions 202 yield 8,701,827 observed pSNVs, which form the final benign set 302, according to one implementation. In some implementations, the benign pSNVs are observed in human and non-human primate species such as chimpanzee, bonobo, gorilla, orangutan, rhesus, and marmoset.

In some implementations, the criterion for inclusion in the benign set is that the minor allele frequency of an observed pSNV should be greater than 0.1%. Such a criterion produces 600,000 observed pSNVs, according to one implementation. In other implementations, the inclusion criterion does not take into account the minor allele frequencies of observed pSNVs. That is, as long as a pSNV is observed in human and the non-human primate species, it is included in the benign set and thus labeled as benign. The second inclusion strategy produces the much larger benign set of 8,701,827 observed pSNVs, according to one implementation.

Further, from the 59,455,812 total base positions 201, 15,406,835 unobserved pSNV positions 203 are removed that belong to homopolymer regions, low-complexity regions, and overlapping coding positions (e.g., start or stop codons), which are considered either unreliable due to sequence-specific errors or irrelevant to the analysis of non-coding variants.

Thus, in some implementations, what results is 36,000,000 unobserved pSNV positions 204, from which a total of 108,000,000 unobserved pSNVs 205 are derived by mutating each of the 36,000,000 loci to the three alternative single-base alleles. These 108,000,000 unobserved pSNVs form the final pool 205 of substitutionally generated unobserved pSNVs, according to one implementation.

Semi-Supervised Training

Because semi-supervised learning algorithms use both labeled and unlabeled instances in the training process, they can produce classifiers that achieve better performance than completely supervised learning algorithms that have only a small amount of labeled data available for training. The principle behind semi-supervised learning is that intrinsic knowledge within unlabeled data can be leveraged in order to strengthen the prediction capability of a supervised model that only uses labeled instances, thereby providing a potential advantage for semi-supervised learning. Model parameters learned by a supervised classifier from a small amount of labeled data may be steered towards a more realistic distribution (which more closely resembles the distribution of the test data) by the unlabeled data.

Another challenge that is prevalent in bioinformatics is the data imbalance problem. The data imbalance phenomenon arises when one of the classes to be predicted is underrepresented in the data because instances belonging to that class are rare (noteworthy cases) or hard to obtain. Ironically, minority classes are typically the most important to learn, because they may be associated with special cases.

An algorithmic approach to handle imbalanced data distributions is based on ensembles of classifiers. Limited amounts of labeled data naturally lead to weaker classifiers, but ensembles of weak classifiers tend to surpass the performance of any single constituent classifier. Moreover, ensembles typically improve the prediction accuracy obtained from a single classifier by a factor that validates the effort and cost associated with learning multiple models. Intuitively, aggregating several classifiers leads to better overfitting control, since averaging the high variability of individual classifiers also averages the classifiers' overfitting.

Figure 3:
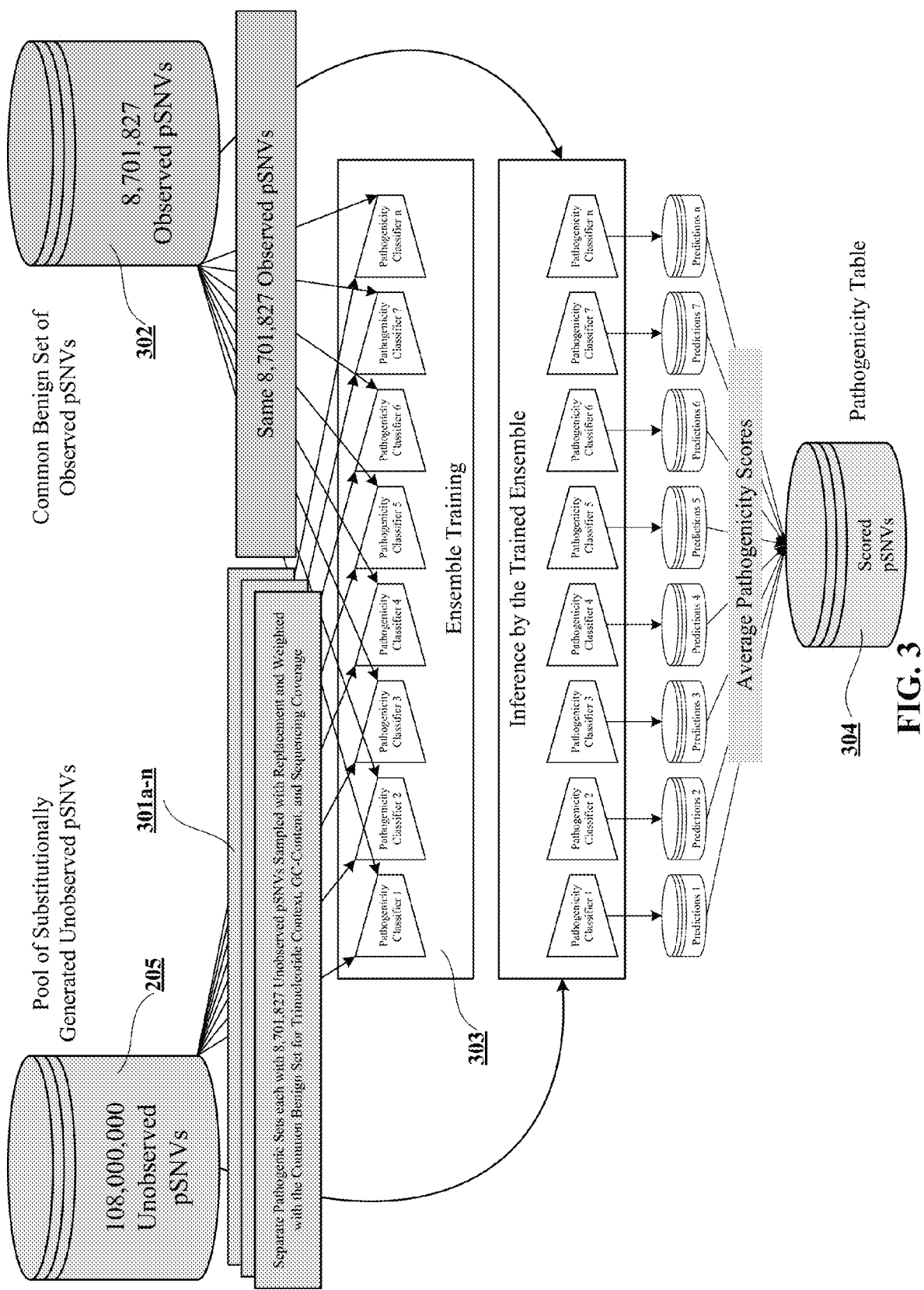
FIG. 3 illustrates one implementation of training the pathogenicity classifiers and application of the trained pathogenicity classifiers on inference data.

FIG. 3 illustrates one implementation of training the pathogenicity classifiers and application of the trained pathogenicity classifiers on inference data. Existing labeled databases have a non-trivial number of entries, after removing variants of uncertain significance, there are only few variants remaining with non-conflicting interpretations of pathogenicity. Systematic reviews have also found that these entries often have insufficient clinical evidence to support their annotated pathogenicity. Additionally, most of the variants in human curated databases tend to be within a very small set of genes, making them mismatched for variants in benign training datasets, which are ascertained genome-wide using human common variants or chimpanzee-human fixed substitutions. Given how differently the datasets were ascertained, training a supervised learning model with human-curated variants as the pathogenic set and genome-wide common variants as the benign set was considered to introduce significant biases.

In some implementations, the ensemble 303 of pathogenicity classifiers can be trained to discriminate between a common benign set 302 of observed pSNVs and separate pathogenic sets 301a-n of unobserved pSNVs sampled with replacement from the pool 205 of substitutionally generated unobserved pSNVs. The ensemble 303 can contain any number of pathogenicity classifiers, e.g., in the range of 1 to 200. In some implementations, at least 10 pathogenicity classifiers produce improved results. Improvements taper off, exhibiting diminishing returns as the number of pathogenicity classifiers increases to 100 or 200. Adding pathogenicity classifiers produces marginal improvement, without representing a different approach, at least beyond 100 pathogenicity classifiers.

The pool 205 of substitutionally generated unobserved pSNVs and, by extension, separate pathogenic sets 301a-n sampled from the pool 205 contain a mixture of benign and pathogenic pSNVs; however, for training purposes, their constituent variants are assigned a pathogenic label 507. Also, the separate pathogenic sets 301a-n are matched with the common benign set 302 by weighted sampling to remove biases. In some implementations, the pool 205 of substitutionally generated unobserved pSNVs can be referred to as the unlabeled set and the separate pathogenic sets 301a-n can be referred to as respectively sampled unlabeled sets.

In one implementation, the common benign set 302 of 8,701,827 observed pSNVs includes human variants from the ExAC/gnomAD database and variants from six species of non-human primates. The separate pathogenic sets 301a-n are respectively matched with the benign variants by weighted sampling based on trinucleotide context distribution and local GC-content distribution (to control for mutational rate, genetic drift, and gene conversion), and sequence coverage distribution (to adjust for the impact of alignability and sequence coverage on variant ascertainment).

Figure 4:
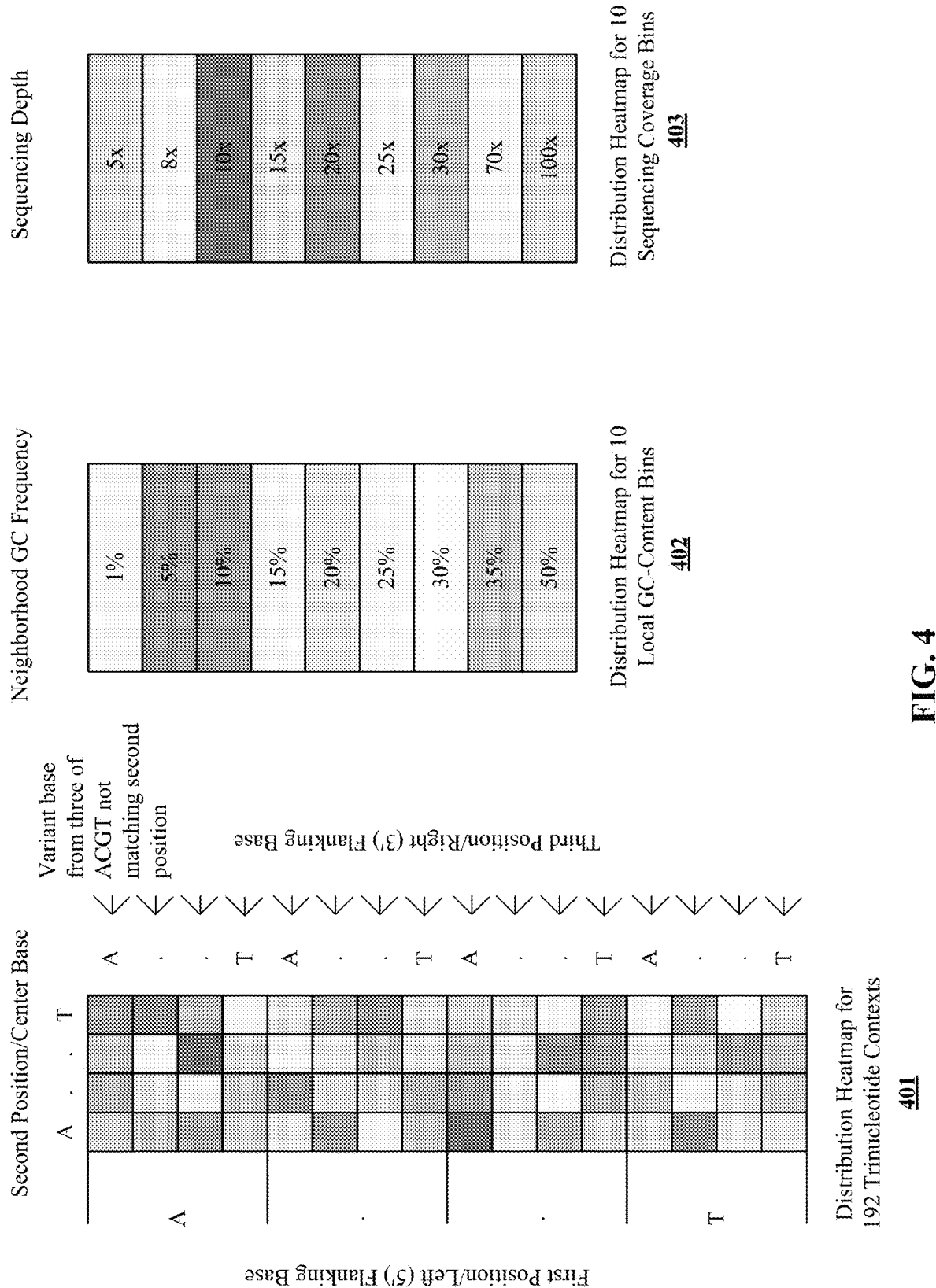
FIG. 4 illustrates one implementation of trinucleotide context, local GC-content, and sequencing coverage distribution heatmaps of the observed pSNVs in the common benign set. Weighted sampling is used to draw the separate pathogenic sets of unobserved pSNVs from the pool of substitutionally generated unobserved pSNVs so that these distributions substantially match between the pathogenic sets and the common benign set.

FIG. 4 illustrates one implementation of trinucleotide context 401, local GC-content 402, and sequencing coverage 403 distribution heatmaps of the observed pSNVs in the common benign set 302. Weighted sampling is used to draw the separate pathogenic sets 301a-n of unobserved pSNVs from the pool 205 of substitutionally generated unobserved pSNVs so that these distributions 401, 402, and 403 substantially match between the pathogenic sets 301a-n and the common benign set 302.

In FIG. 4, first an example distribution heatmap 401 of 192 possible combinations of bases is shown, corresponding to the first position or left (5') flanking base, the second position or center base, the third position or right (3') flanking base, and the variant base from three of ACGT not matching the second position. The trinucleotide is formed by the base before the variant, the reference base of the variant, and the base after the variant. The reference base of the variant can be changed into the other three nucleotides. In total, there are 64×3=192 trinucleotide contexts. In other implementations, a trinucleotide context and its reverse complement are considered the same and the number of trinucleotide contexts are reduced to 96. That is, some of the 64×3=192 trinucleotide contexts are considered identical and are merged. Accordingly, the illustrated distribution accounts for position-specific and base-specific mutations. For example, "ACG" mutating to "AGG" is assigned its own distribution and so is "AAG". Then, an example distribution heatmap 402 for 10 local GC-content bins is depicted. Local GC-content can be expressed for a window (e.g., 300 bases) around a target pSNV as a percentage frequency or as a fractional value between 0 and 1. Finally, an example distribution heatmap 403 for 10 sequencing coverage bins is shown. The illustrated implementation creates 6400 possible bands (64 trinucleotide contexts×10 GC-content bins×10 sequencing coverage bins) that can be used to perform the weighted sampling.

The common benign set 302 and each of the pathogenic sets 301a-n can have a same size, i.e., the size of each pathogenic set is 8,701,827 unobserved pSNVs. The weighted sampling results in the pathogenic sets 301a-n having some common, overlapping unobserved pSNVs within a pathogenic set across sampling cycles and across pathogenic sets 301a-n for a current sampling cycle. This results in the pathogenicity classifiers having multiple initializations of the same unobserved pSNV, which in turn strengths their classification power.

In some implementations, the pathogenicity classifiers are trained over one or more epochs on a pathogenic set sampled at the current sampling cycle. The training can continue on one or more additional pathogenic sets sampled at one or more successive sampling cycles. The training is concluded when the pathogenicity classifiers' pathogenicity score predictions on a validation set having held-out observed pSNVs and unobserved pSNVs form substantially discrete probability distribution clusters of benign and pathogenic predictions.

Classifier parameters derived from the training are stored in memory. The trained classifiers are applied to produce pathogenicity scores for at least some unobserved pSNVs in the pool of substitutionally generated unobserved pSNVs. For each unobserved pSNV in the at least some unobserved pSNVs, an average and/or maximum pathogenicity score is determined from the pathogenicity scores produced by the trained pathogenicity classifiers. Then, a pathogenicity table 304 is generated that identifies the average and/or maximum pathogenicity score for each unobserved pSNV in the at least some unobserved pSNVs.

In some implementations, the trained classifiers are also applied to produce pathogenicity scores for at least some observed pSNVs in the common benign set of observed pSNVs. For each observed pSNV in the at least some observed pSNVs, an average and/or maximum pathogenicity score is determined from the pathogenicity scores produced by the trained pathogenicity classifiers. Then, the pathogenicity table 304 is generated that identifies the average and/or maximum pathogenicity score for each observed pSNV in the at least some observed pSNVs.

Sparsely Encoded Ground Truth Data

Figure 5:
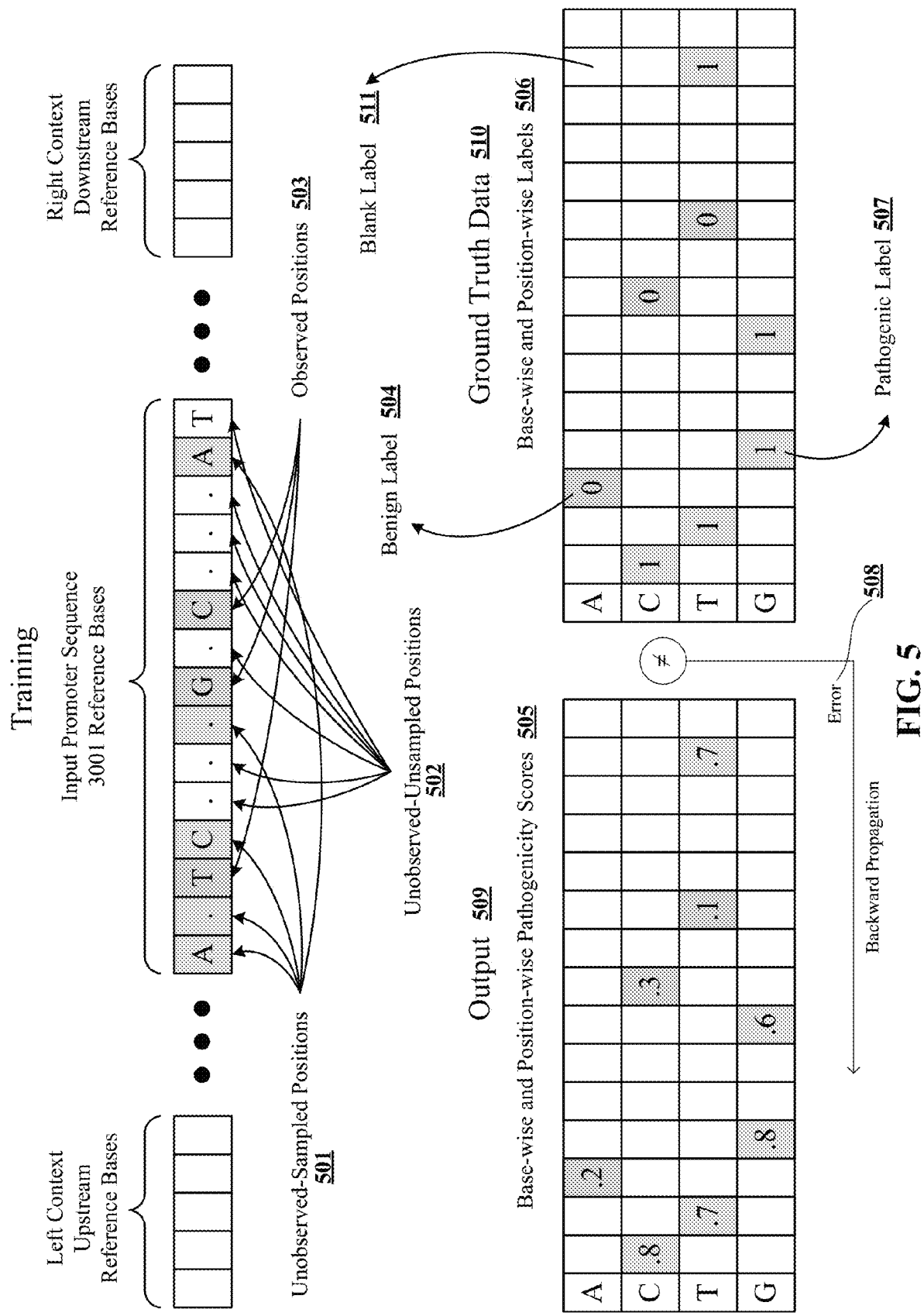
FIG. 5 is one implementation of training the pathogenicity classifiers using sparsely encoded ground truth data that has base-wise and position-wise labels for observed positions, unobserved-sampled positions, and unobserved-unsampled positions in input promoter sequences.

FIG. 5 is one implementation of training the pathogenicity classifiers using sparsely encoded ground truth data 510 that has base-wise and position-wise labels 506 for observed positions 503, unobserved-sampled positions 501, and unobserved-unsampled positions 502 in input promoter sequences. The input promoter sequences cover the observed pSNVs in the common benign set 302 and contain reference bases at the observed positions 503, the unobserved-sampled positions 501, and the unobserved-unsampled positions 502. The observed positions 503 are positions at which the observed pSNVs in the common benign set 302 occurred (in green). The unobserved positions 601 are positions at which the substitutionally generated unobserved pSNVs in the pool 205 are located. The unobserved-sampled positions 501 are positions at which the unobserved pSNVs sampled for a particular classifier at a current sampling cycle are located (in blue). The unobserved-unsampled positions 502 are positions at which some of the substitutionally generated unobserved pSNVs not sampled for the particular classifier at the current sampling cycle are located (in white).

A ground truth data generator (not shown) then generates the ground truth data 510 with base-wise and position-wise labels 506 for each input promoter sequence. For the observed positions 503, the ground truth data 510 assigns a blank label 511 to bases that match the reference bases, assigns the blank label 511 to bases that are variations from the reference bases which do not match the observed pSNVs, and assigns a benign label 504 to bases that are variations from the reference bases which match the observed pSNVs. For the unobserved-sampled positions 501, the ground truth data 510 assigns the blank label 511 to bases that match the reference bases, assigns the blank label 511 to bases that are variations from the reference bases which do not match the unobserved pSNVs, and assigns a pathogenic label 507 to bases that are variations from the reference bases which match the unobserved pSNVs. For the unobserved-unsampled positions 502, the ground truth data 510 assigns the blank label 511 to all bases.

In some implementations, scores for the labels 506 are generated by a softmax classification layer and use (0, 1) softmax encoding for the pathogenic label 507, (1, 0) softmax encoding for the benign label 504, and (0, 0) softmax encoding for the blank label 511.

A trainer (not shown) then uses a gradient update training technique to train the pathogenicity classifiers to generate, in response to processing the input promoter sequences, outputs with base-wise and position-wise pathogenicity scores 505 that progressively approach corresponding base-wise and position-wise labels 506 in the ground truth data 510. In some implementations, the trainer iteratively optimizes a loss function that minimizes error between the base-wise and position-wise pathogenicity scores 505 in the outputs and the corresponding base-wise and position-wise labels 506 in the ground truth data 510 and iteratively updates parameters of the classifiers based on the error 508 using backpropagation.

Furthermore, for positions in the input promoter sequences, a protein binding affinity score is encoded. These scores are determined by one or more protein binding affinity predictors that are pre-trained on positive training examples of protein binding motifs and negative training examples of non-binding motifs to generate a position-wise protein binding affinity score sequence in response to processing an input sequence. The predictors can produce scores for hundreds of proteins in multiple different conditions and/or cell types.

Additionally, for positions in the input promoter sequences, a DNA accessibility inducing score is encoded. These scores are determined by one or more DNA accessibility predictors that are pre-trained on positive training examples of DNA accessibility inducing motifs and negative training examples of non-inducing motifs to generate a position-wise DNA accessibility inducing score sequence in response to processing an input sequence. The predictors can produce scores for hundreds of DNA samples in multiple different conditions and/or cell types.

Inference

Figure 6:
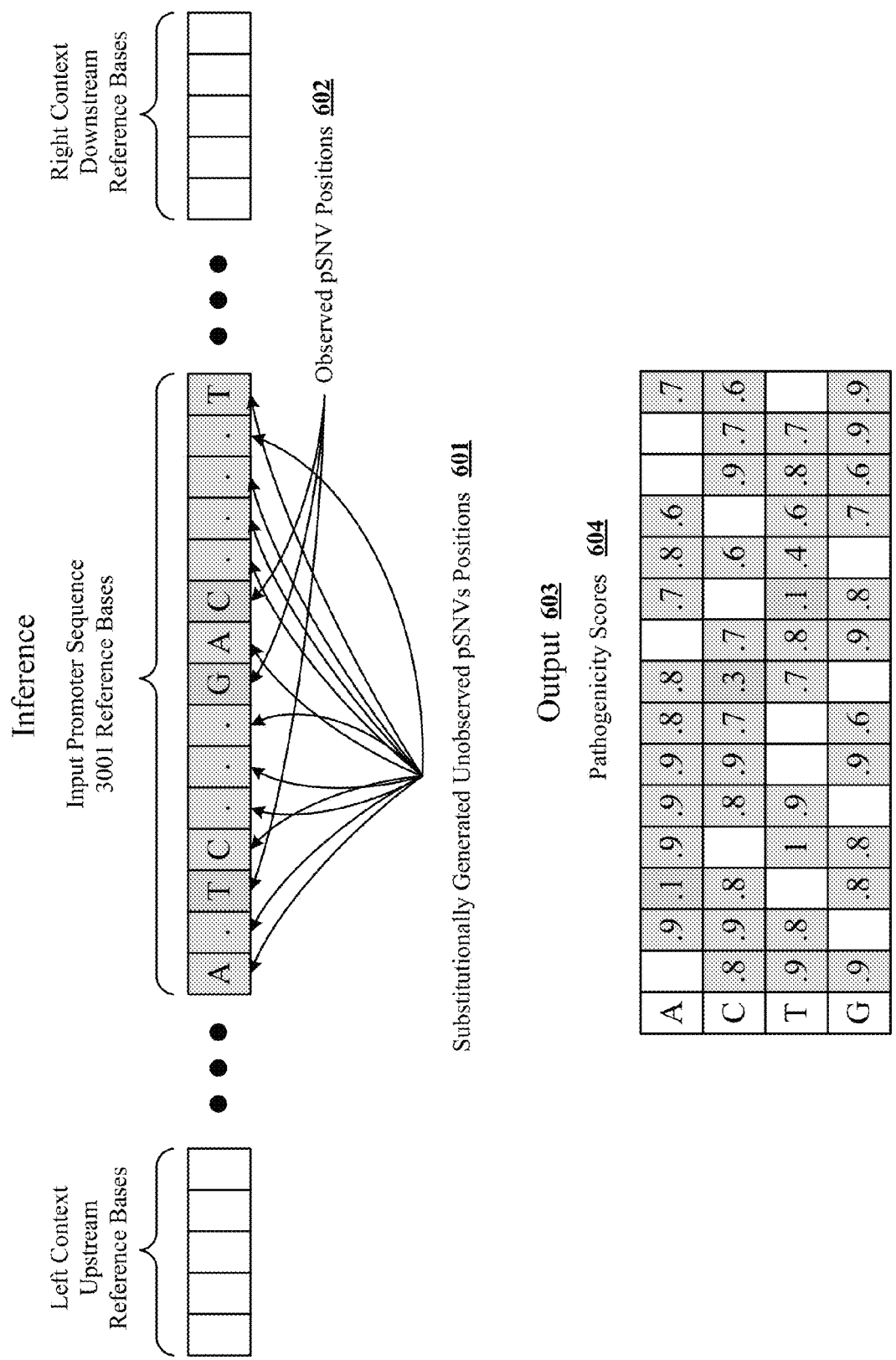
FIG. 6 shows one implementation of how the trained pathogenicity classifiers classify, as benign or pathogenic, base variations from reference bases occurring in the input promoter sequences at positions covering observed pSNVs and substitutionally generated unobserved pSNVs.

FIG. 6 shows one implementation of how the trained pathogenicity classifiers classify, as benign or pathogenic, base variations from reference bases occurring in the input promoter sequences at positions 602 covering observed pSNVs in the common benign set 302 and positions 601 substitutionally generated unobserved pSNVs in the pool 205.

The pathogenicity classifiers have a modified WaveNet-style architecture that iterating over particular locations in an input promoter sequence and over three base variations from a reference base found at a particular location. The modified WaveNet-style architecture can calculate up to 9,000 outputs for 3,000 locations in the input, as each location has up to three single base variations. The modified WaveNet-style architecture scales relatively well, because intermediate calculations are reused. The pathogenicity classifiers determine in a single invocation of the modified WaveNet-like architecture pathogenicity likelihood scores for at least one of the three base variations at a multiplicity of the particular locations in the input promoter sequence and store the pathogenicity likelihood scores determined in the single invocation. The determining of at least one of the three base variations further includes determining all of the three variations. The multiplicity of the particular locations is at least 500 or 1,000, or 1500, or 2000, or ninety percent of the input promoter sequence.

A trained pathogenicity classifier comprises an input module (not shown) that accepts an input promoter sequence with reference bases at positions 602 covering observed pSNVs in the common benign set 302 and positions 601 substitutionally generated unobserved pSNVs in the pool 205.

The trained pathogenicity classifier also comprises a processing module (not shown) that processes the input promoter sequence through one or more layers of the pathogenicity classifier to generate an alternative representation of the input promoter sequence. In some implementations, when the trained pathogenicity classifier is a deep convolutional neural network, the layers are convolution layers with convolution filters and the alternative representation is a convolved representation. In other implementations, when the trained pathogenicity classifier is a recurrent neural network, the layers are recurrent units with gates and the alternative representation is a hidden representation.

The trained pathogenicity classifier further comprises an output module (not shown) that processes the alternative representation to generate an output 603 which, for each position in the input promoter sequence, classifies each of three base variations from a corresponding reference base as benign or pathogenic. In some implementations, the output includes pathogenicity likelihood scores 604 for each of the three base variations.

The trained pathogenicity classifier receives supplemental input from a protein binding affinity sub-classifier that encodes a protein binding affinity score to each position in the input promoter sequence. The trained pathogenicity classifier also receives supplemental input from a DNA accessibility sub-classifier that encodes a DNA accessibility inducing score to each position in the input promoter sequence.

Deep Learning Architecture

Regarding pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, a powerful computational model for predicting the pathogenicity of non-coding variants can have enormous benefit for both basic science and translational research because over 98% of the human genome is non-coding and it is estimated that 93% of disease-associated variants lie in these regions.

In some implementations, pathogenicity classifiers can be based on the architecture of residual blocks. The residual blocks comprise repeating units of convolution, interspersed with skip connections that allow information from earlier layers to skip over residual blocks. In each residual block, the input layer is first batch normalized, followed by an activation layer using rectified linear units (ReLU). The activation is then passed through an atrous convolution layer. This intermediate output from the atrous convolution layer is again batch normalized and ReLU activated, followed by another atrous convolution layer. At the end of the second atrous convolution layer, we summed its output with the original input into the residual block, which acts as a skip connection by allowing the original input information to bypass the residual block. In such an architecture, termed a deep residual learning network by its authors, the input is preserved in its original state and the residual connections are kept free of nonlinear activations from the model, allowing effective training of deeper networks.

Following the residual blocks, a softmax layer computes probabilities that translate to either the pathogenic label, the benign label, or the blank label. In some implementations, the pathogenicity classifiers are trained with accumulated categorical cross entropy loss function using the ADAM optimizer.

Figure 7:
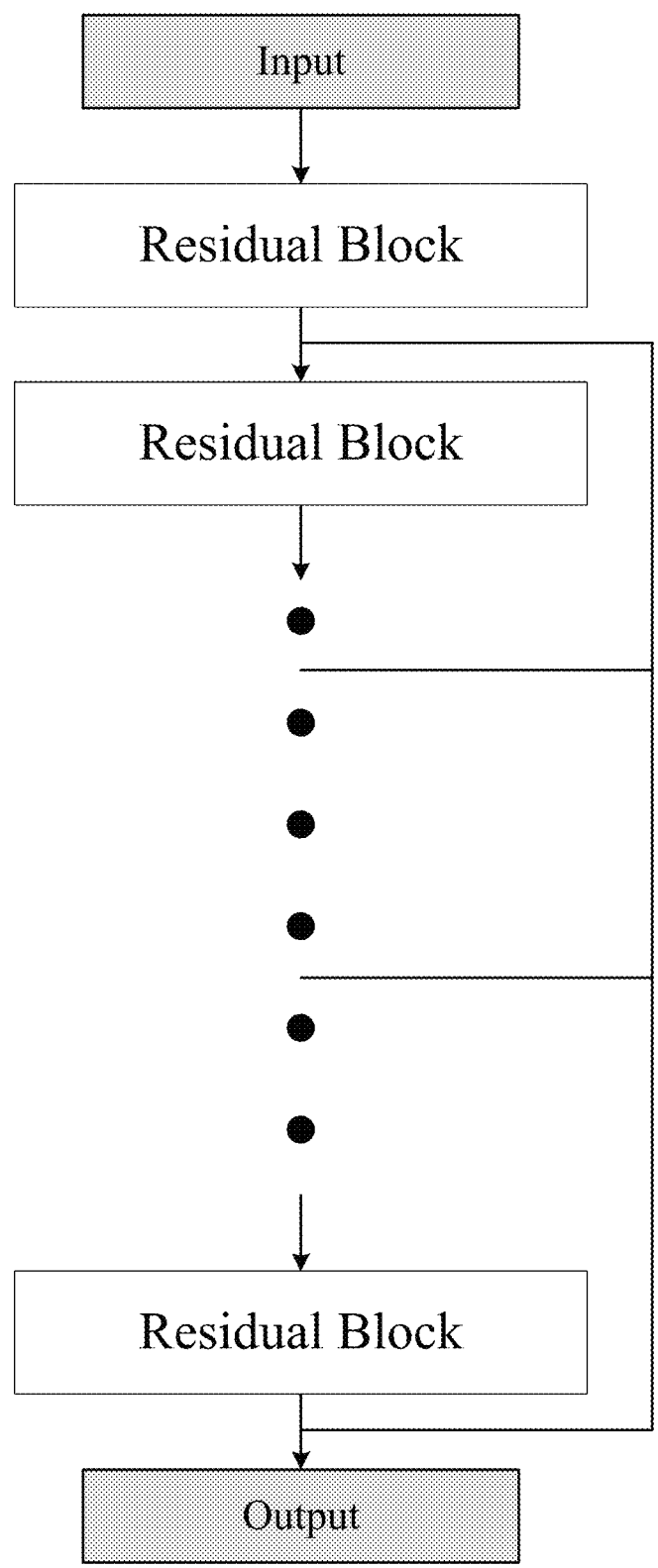
FIG. 7 illustrates one implementation of a deep convolutional neural network-based architecture template that is used to construct the pathogenicity classifiers.
Figure 8:
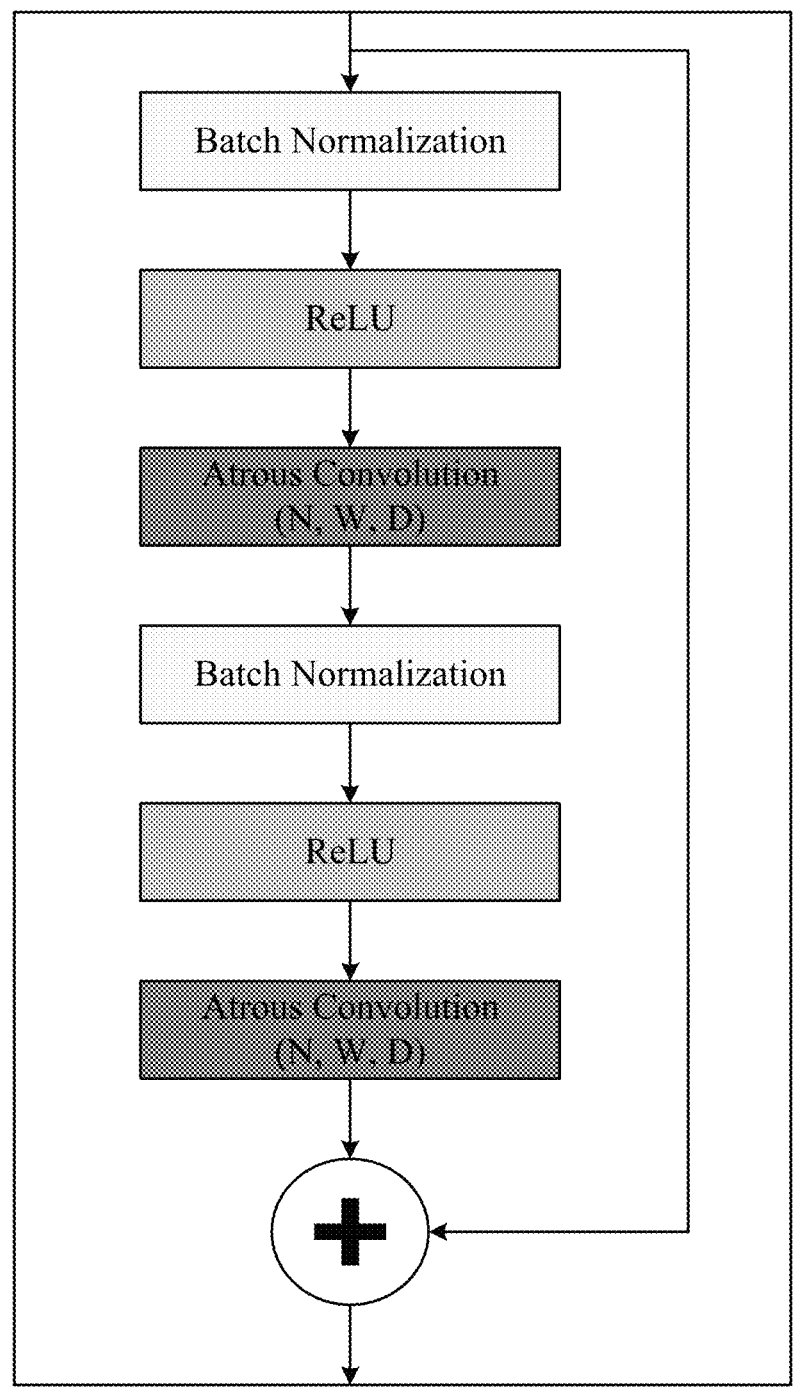
FIG. 8 depicts one implementation of a residual block that is part of the deep convolutional neural network architecture of FIG. 6.

FIG. 7 illustrates one implementation of a deep convolutional neural network-based architecture template that is used to construct the pathogenicity classifiers. FIG. 8 depicts one implementation of a residual block that is part of the deep convolutional neural network architecture of FIG. 7. In some implementations, the pathogenicity classifiers are deep convolutional neural networks that contain groups of residual blocks arranged in a sequence from lowest to highest. Each group of residual blocks is parameterized by a number of convolution filters in the residual blocks, a convolution window size of the residual blocks, and an atrous convolution rate of the residual blocks. The atrous convolution rate progresses non-exponentially from a lower residual block group to a higher residual block group, in some implementations. In other implementations, it progresses exponentially. The size of convolution window varies between groups of residual blocks, and each residual block comprises at least one batch normalization layer, at least one rectified linear unit (abbreviated ReLU) layer, at least one atrous convolution layer, and at least one residual connection.

In some implementations, the dimensionality of the input is $(C^u+L+C^d) \times 4$, where $C^u$ is a number of upstream flanking context bases, $C^d$ is a number of downstream flanking context bases, and L is a number of bases in the input promoter sequence. The dimensionality of the output is $4 \times L$.

In some implementations, each group of residual blocks produces an intermediate output by processing a preceding input and the dimensionality of the intermediate output is $(I-[\{(W-1)*D\}*A]) \times N$, where I is dimensionality of the preceding input, W is convolution window size of the residual blocks, D is atrous convolution rate of the residual blocks, A is a number of atrous convolution layers in the group, and N is a number of convolution filters in the residual blocks.

Figure 9:
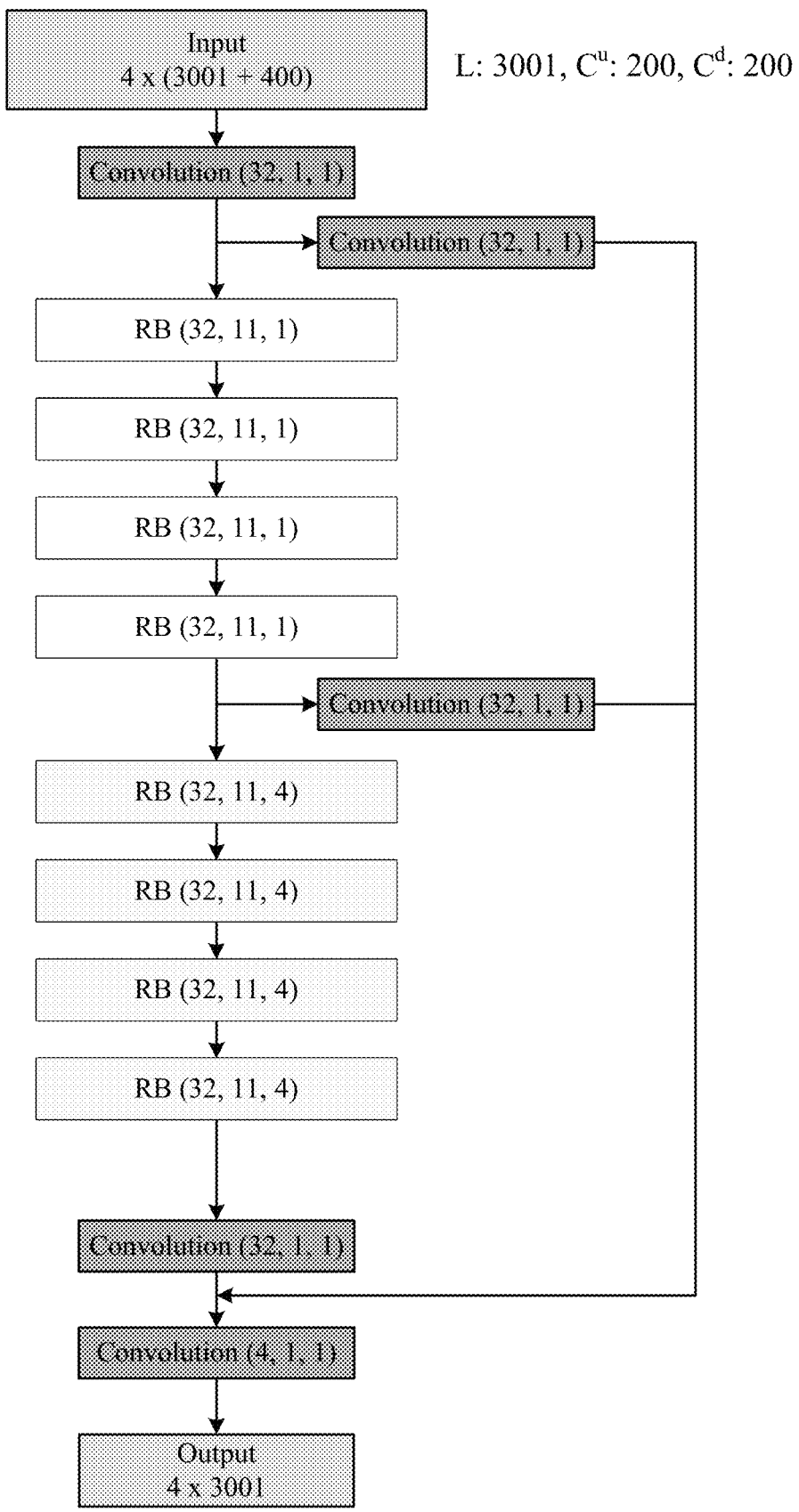
FIG. 9 is an example deep convolutional neural network-based architecture used to construct the pathogenicity classifiers.

FIG. 9 is an example deep convolutional neural network-based architecture used to construct the pathogenicity classifiers. This architecture is used when the input has 200 upstream flanking context bases ($C^u$) to the left of the input sequence and 200 downstream flanking context bases ($C^d$) to the right of the input sequence. The length of the input sequence (L) can be arbitrary, such as 3001.

In this architecture, each residual block in a first group has 32 convolution filters, 11 convolution window size, and 1 atrous convolution rate and each residual block in a second group has 32 convolution filters, 11 convolution window size, and 4 atrous convolution rate.

In other architectures, each residual block has 32 convolution filters, 11 convolution window size, and 1 atrous convolution rate.

Figure 10:
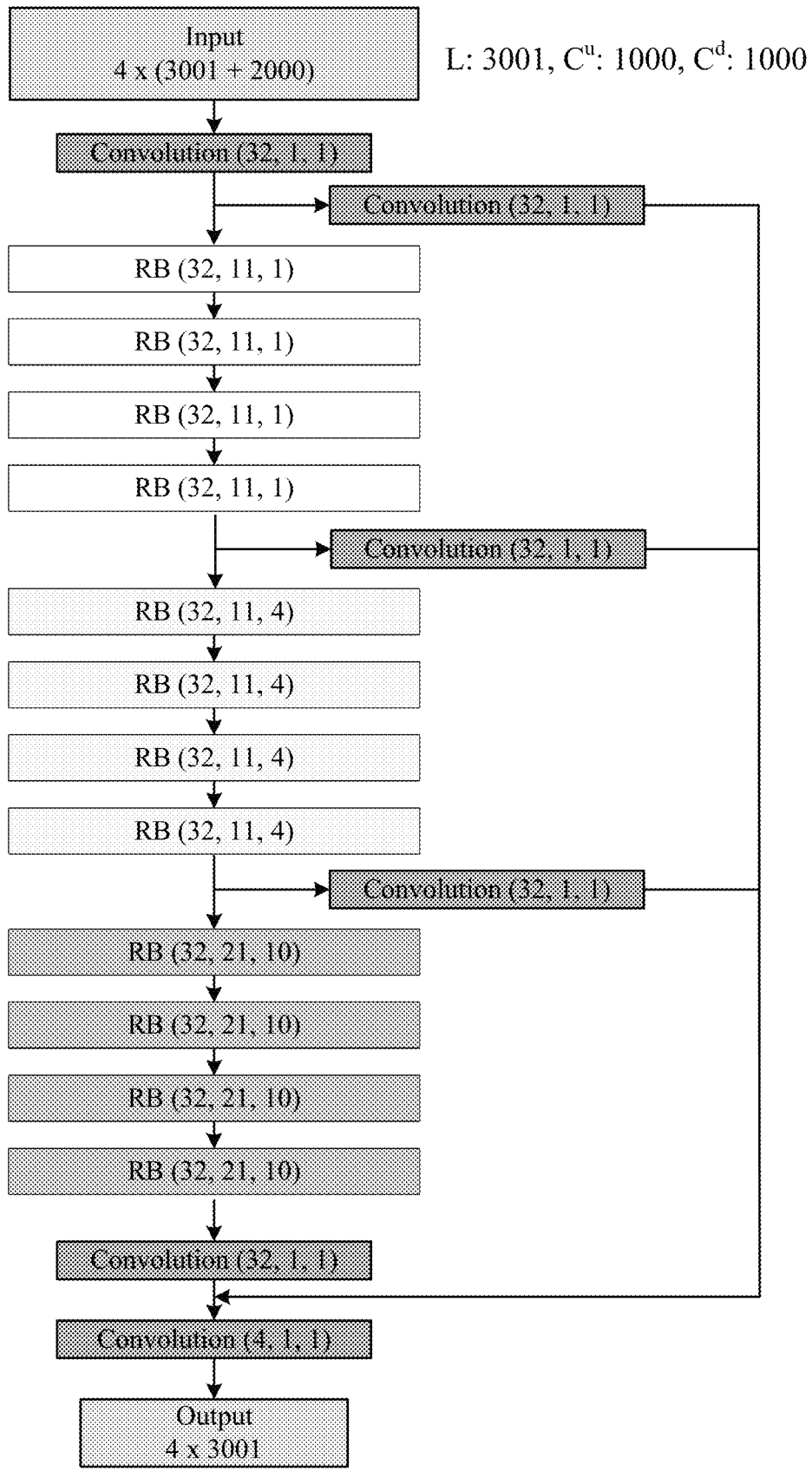
FIG. 10 is another example deep convolutional neural network-based architecture used to construct the pathogenicity classifiers.

FIG. 10 is another example deep convolutional neural network-based architecture used to construct the pathogenicity classifiers. This architecture is used when the input has 1000 upstream flanking context bases ($C^u$) to the left of the input sequence and 1000 downstream flanking context bases ($C^d$) to the right of the input sequence. The length of the input sequence (L) can be arbitrary, such as 3001.

In this architecture, there are at least three groups of four residual blocks and at least three skip connections. Each residual block in a first group has 32 convolution filters, 11 convolution window size, and 1 atrous convolution rate, each residual block in a second group has 32 convolution filters, 11 convolution window size, and 4 atrous convolution rate, and each residual block in a third group has 32 convolution filters, 21 convolution window size, and 19 atrous convolution rate.

FIG. 11 is yet another example deep convolutional neural network-based architecture used to construct the pathogenicity classifiers. This architecture is used when the input has 5000 upstream flanking context bases ($C^u$) to the left of the input sequence and 5000 downstream flanking context bases ($C^d$) to the right of the input sequence. The length of the input sequence (L) can be arbitrary, such as 3001.

In this architecture, there are at least four groups of four residual blocks and at least four skip connections. Each residual block in a first group has 32 convolution filters, 11 convolution window size, and 1 atrous convolution rate, each residual block in a second group has 32 convolution filters, 11 convolution window size, and 4 atrous convolution rate, each residual block in a third group has 32 convolution filters, 21 convolution window size, and 19 atrous convolution rate, and each residual block in a fourth group has 32 convolution filters, 41 convolution window size, and 25 atrous convolution rate.

Training

Figure 13A:
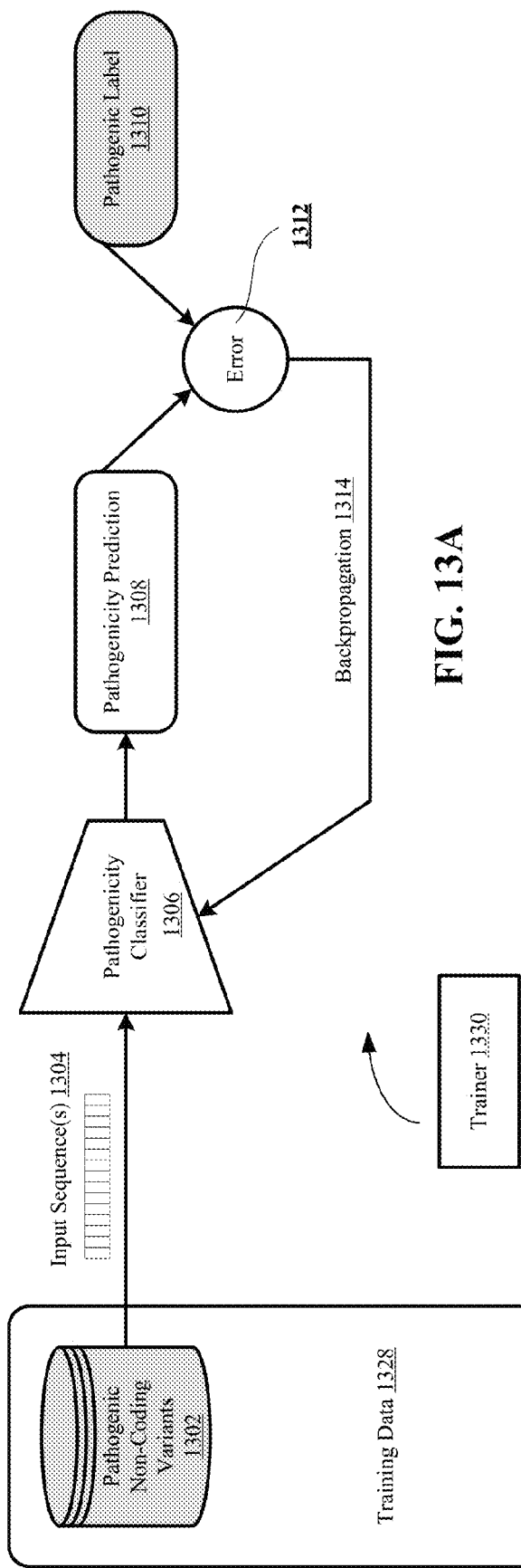
FIG. 13A illustrates one implementation of training an example pathogenicity classifier using a pathogenic non-coding variant that is annotated with a pathogenic label.
Figure 13B:
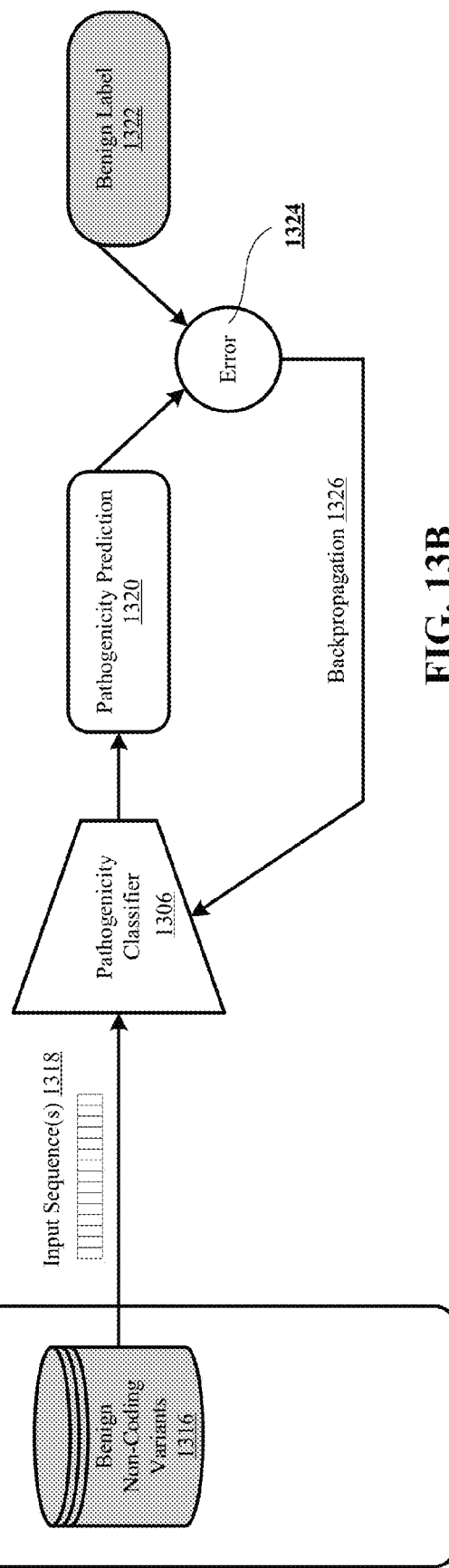
FIG. 13B depicts one implementation of training the pathogenicity classifier using a benign non-coding variant that is annotated with a benign label.

FIGS. 13A and 13B show training of an example pathogenicity classifier 1306. In one implementation, the pathogenicity classifier 1306 is a convolutional neural network. In another implementation, the pathogenicity classifier 1306 is a recurrent neural network. In yet another implementation, the pathogenicity classifier 1306 is a residual neural network with residual bocks and residual connections. In a further implementation, the pathogenicity classifier 1306 is a combination of a convolutional neural network and a recurrent neural network.

One skilled in the art will appreciate that the pathogenicity classifier 1306 can use various padding and striding configurations. It can use different output functions (e.g., classification or regression) and may or may not include one or more fully-connected layers. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The pathogenicity classifier 1306 is trained using training data 1328. The training data 1328 includes a pathogenic set of non-coding variants 1302 that are annotated with a pathogenic label 1310 and a benign set of non-coding variants 1316 that are annotated with a benign label 1322.

FIG. 13A illustrates one implementation of training the pathogenicity classifier 1306 using a pathogenic non-coding variant that is annotated with the pathogenic label 1310.

The pathogenicity classifier 1306 processes one or more input sequences 1304 associated with a particular pathogenic non-coding variant 1302a (not shown) that is selected from the pathogenic set of non-coding variants 1302. The input sequences 1304 are processed through the pathogenicity classifier 1306, which in response produces a pathogenicity prediction 1308 for the particular pathogenic non-coding variant 1302a.

A trainer 1330 modifies weights of the pathogenicity classifier 1306 using backpropagation 1314 based on an error 1312 computed between the pathogenicity prediction 1308 made for the particular pathogenic non-coding variant 1302a and the pathogenic label 1310.

In one implementation, the input sequence 1304 is a reference sequence that contains, at a target position, a reference non-coding base which is flanked by downstream and upstream context non-coding bases. In one implementation, the input sequence 1304 is an alternative sequence that contains, at the target position, the particular pathogenic non-coding variant 1302*a* which is flanked by the downstream and upstream context non-coding bases. In some implementations, both the reference and alternative sequences are fed as input to the pathogenicity classifier 1306.

In one implementation, the input sequence 1304 is a metadata sequence that characterizes metadata about the particular pathogenic non-coding variant 1302*a*. In some implementations, the metadata sequence is generated by a neural network (e.g., a sequence-to-sequence model like WaveNet). In some implementations, the metadata is associated with epigenetic signals, including deoxyribonucleic acid (DNA) methylation changes, histone modifications, noncoding ribonucleic acid (ncRNA) expression, chromatin structural changes, deoxyribonuclease (DNase), and histone 3 lysine 27 acetylation (H3K27ac).

In one implementation, the input sequence 1304 is a non-coding sequence that contains some reference non-coding bases, the particular pathogenic non-coding variant 1302*a*, and some additional non-coding variants.

FIG. 13B depicts one implementation of training the pathogenicity classifier 1306 using a benign non-coding variant that is annotated with the benign label 1322.

The pathogenicity classifier 1306 processes one or more input sequences 1318 associated with a particular benign non-coding variant 1316*a* (not shown) that is selected from the benign set of non-coding variants 1316. The input sequences 1318 are processed through the pathogenicity classifier 1306, which in response produces a pathogenicity prediction 1320 for the particular benign non-coding variant 1316*a*.

A trainer 1330 modifies weights of the pathogenicity classifier 1306 using backpropagation 1326 based on an error 1324 computed between the pathogenicity prediction 1320 made for the particular benign non-coding variant 1316*a* and the benign label 1322.

In one implementation, the input sequence 1318 is a reference sequence that contains, at a target position, a reference non-coding base which is flanked by downstream and upstream context non-coding bases. In one implementation, the input sequence 1318 is an alternative sequence that contains, at the target position, the particular benign non-coding variant 1316*a* which is flanked by the downstream and upstream context non-coding bases. In some implementations, both the reference and alternative sequences are fed as input to the pathogenicity classifier 1306.

In one implementation, the input sequence 1318 is a metadata sequence that characterizes metadata about the particular benign non-coding variant 1316*a*. In some implementations, the metadata sequence is generated by a neural network (e.g., a sequence-to-sequence model like WaveNet). In some implementations, the metadata is associated with epigenetic signals, including deoxyribonucleic acid (DNA) methylation changes, histone modifications, noncoding ribonucleic acid (ncRNA) expression, chromatin structural changes, deoxyribonuclease (DNase), and histone 3 lysine 27 acetylation (H3K27ac).

In one implementation, the input sequence 1318 is a non-coding sequence that contains some reference non-coding bases, the particular benign non-coding variant 1316*a*, and some additional non-coding variants.

Computer System

Figure 14:
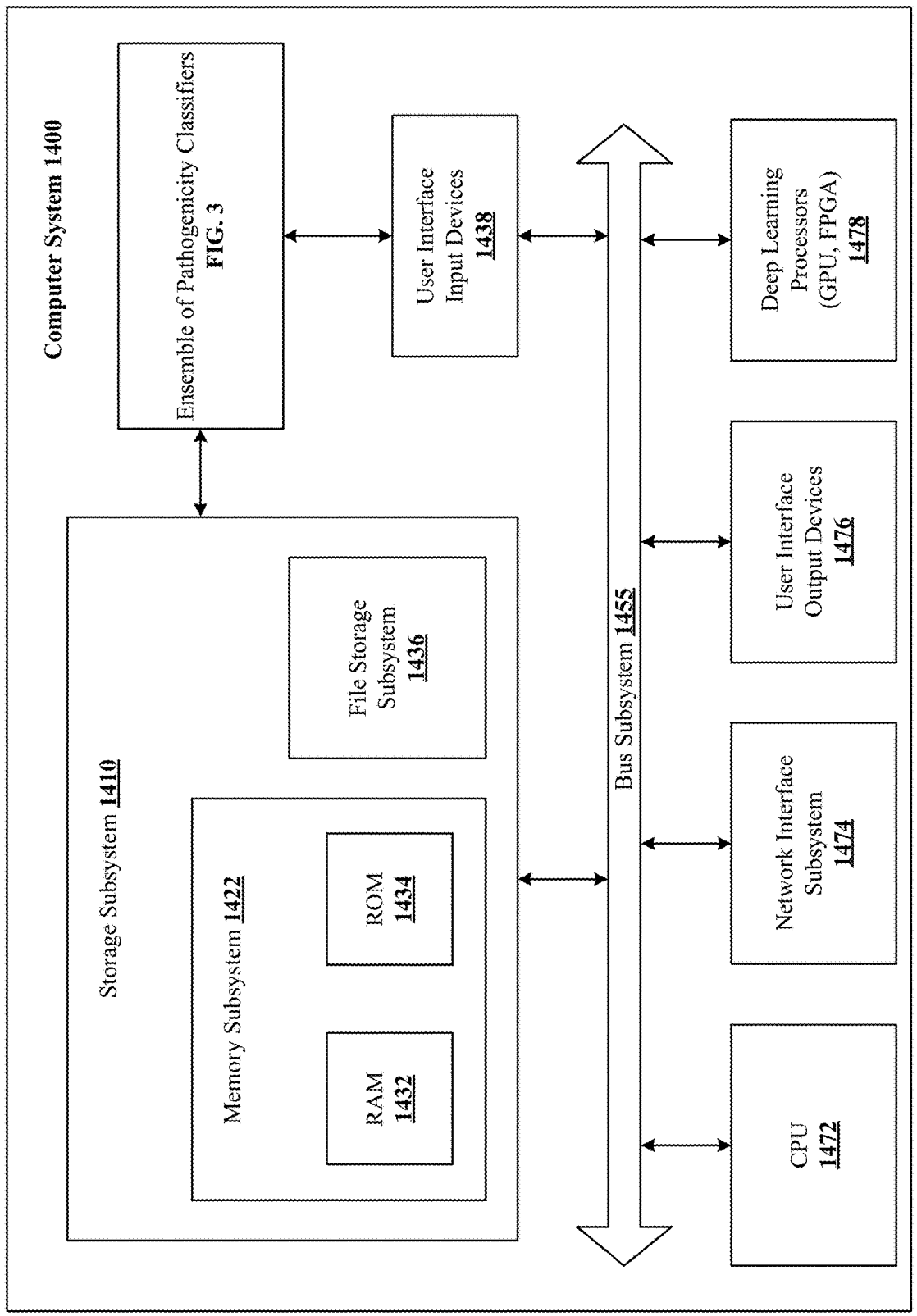
FIG. 14 is a simplified block diagram of a computer system that can be used to implement the ensemble of pathogenicity classifiers.

FIG. 14 is a simplified block diagram of a computer system 1400 that can be used to implement the ensemble of pathogenicity classifiers. Computer system 1400 includes at least one central processing unit (CPU) 1472 that communicates with a number of peripheral devices via bus subsystem 1455. These peripheral devices can include a storage subsystem 1410 including, for example, memory devices and a file storage subsystem 1436, user interface input devices 1438, user interface output devices 1476, and a network interface subsystem 1474. The input and output devices allow user interaction with computer system 1400. Network interface subsystem 1474 provides an interface to outside networks, including an interface to corresponding interface devices in other computer systems.

In one implementation, the ensemble of pathogenicity classifiers of FIG. 3 is communicably linked to the storage subsystem 1410 and the user interface input devices 1438.

User interface input devices 1438 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1400.

User interface output devices 1476 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1400 to the user or to another machine or computer system.

Storage subsystem 1410 stores programming and data constructs that provide the functionality of some or all of the modules and methods described herein. Subsystem 1478 can be graphics processing units (GPUs) or field-programmable gate arrays (FPGAs).

Memory subsystem 1422 used in the storage subsystem 1410 can include a number of memories including a main random access memory (RAM) 1432 for storage of instructions and data during program execution and a read only memory (ROM) 1434 in which fixed instructions are stored. A file storage subsystem 1436 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1436 in the storage subsystem 1410, or in other machines accessible by the processor.

Bus subsystem 1455 provides a mechanism for letting the various components and subsystems of computer system 1400 communicate with each other as intended. Although bus subsystem 1455 is shown schematically as a single bus, alternative implementations of the bus subsystem can use multiple busses.

Computer system 1400 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1400 depicted in FIG. 14 is intended only as a specific example for purposes of illustrating the preferred implementations of the present invention. Many other configurations of computer system 1400 are possible having more or less components than the computer system depicted in FIG. 14.

Particular Implementations

The technology disclosed relates to using semi-supervised algorithms to construct deep learning-based pathogenicity classifiers that accurately predict pathogenicity of promoter single nucleotide variants (pSNVs)).

The technology disclosed can be practiced as a system, method, device, product, computer readable media, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A first neural network-based system implementation of the technology disclosed includes one or more processors coupled to memory. The memory is loaded with computer instructions to train an ensemble of classifiers to predict pathogenicity of promoter region single nucleotide variants (abbreviated pSNVs).

The classifiers are trained using a common benign set of observed pSNVs and separate pathogenic sets of unobserved pSNVs sampled with replacement from a pool of substitutionally generated unobserved pSNVs.

The training includes accessing input promoter sequences covering the observed pSNVs that contain reference bases at observed positions, unobserved-sampled positions, and unobserved-unsampled positions. The observed positions are positions at which the observed pSNVs occurred. The unobserved-sampled positions are positions at which the unobserved pSNVs sampled for a particular classifier at a current sampling cycle are located. The unobserved-unsampled positions are positions at which some of the substitutionally generated unobserved pSNVs not sampled for the particular classifier at the current sampling cycle are located.

The training further includes generating ground truth data with base-wise and position-wise labels for each input promoter sequence. For the observed positions, the ground truth data assigns a blank label to bases that match the reference bases, assigns the blank label to bases that are variations from the reference bases which do not match the observed pSNVs, and assigns a benign label to bases that are variations from the reference bases which match the observed pSNVs. For the unobserved-sampled positions, the ground truth data assigns the blank label to bases that match the reference bases, assigns the blank label to bases that are variations from the reference bases which do not match the unobserved pSNVs, and assigns a pathogenic label to bases that are variations from the reference bases which match the unobserved pSNVs. For the unobserved-unsampled positions, the ground truth data assigns the blank label to all bases.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The training further includes using a gradient update training technique to train the pathogenicity classifiers to generate, in response to processing the input promoter sequences, outputs with base-wise and position-wise pathogenicity scores that progressively approach corresponding base-wise and position-wise labels in the ground truth data.

The training further includes sampling from the pool of substitutionally generated unobserved pSNVs such that trinucleotide context distribution substantially matches between the common benign set and each of the pathogenic sets. The training further includes sampling from the pool of substitutionally generated unobserved pSNVs such that local GC-content distribution substantially matches between the common benign set and each of the pathogenic sets. The training further includes sampling from the pool of substitutionally generated unobserved pSNVs such that sequencing coverage distribution substantially matches between the common benign set and each of the pathogenic sets.

The training further includes for positions in the input promoter sequences, encoding a protein binding affinity score determined by one or more protein binding affinity predictors pre-trained on positive training examples of protein binding motifs and negative training examples of non-binding motifs to generate a position-wise protein binding affinity score sequence in response to processing an input sequence.

The training further includes for the positions in the input promoter sequences, encoding a deoxyribonucleic acid (abbreviated DNA) accessibility inducing score determined by one or more DNA accessibility predictors pre-trained on positive training examples of DNA accessibility inducing motifs and negative training examples of non-inducing motifs to generate a position-wise DNA accessibility inducing score sequence in response to processing an input sequence.

The observed pSNVs are included in the common benign set if they have a minor allele frequency greater than 0.1%. The observed pSNVs are included in the common benign set irrespective of their minor allele frequencies. Some of the observed pSNVs in the common benign set are observed in humans. Some of the observed pSNVs in the common benign set are observed in non-human primate species. The common benign set and each of the pathogenic sets have a same size. The pathogenic sets have some common unobserved pSNVs.

The pool of substitutionally generated unobserved pSNVs is qualified to not include some unobserved pSNVs that are part of homopolymer regions, low-complexity regions, and overlapping coding regions.

The training further includes iteratively optimizing a loss function that minimizes error between the base-wise and position-wise pathogenicity scores in the outputs and the corresponding base-wise and position-wise labels in the ground truth data and iteratively updating parameters of the classifiers based on the error (e.g., using backpropagation).

The training further includes training the particular classifier over one or more epochs on a pathogenic set sampled at the current sampling cycle, continuing the training of the particular classifier on one or more additional pathogenic sets sampled at one or more successive sampling cycles, and concluding the training of the particular classifier when the particular classifier's pathogenicity score predictions on a validation set having held-out observed pSNVs and unobserved pSNVs form substantially discrete probability distribution clusters of benign and pathogenic predictions.

The training further includes storing, in memory, classifier parameters derived by the training.

The training further includes applying the trained classifiers to produce pathogenicity scores for at least some unobserved pSNVs in the pool of substitutionally generated unobserved pSNVs, for each unobserved pSNV in the at least some unobserved pSNVs, determining an average and/or maximum pathogenicity score from the pathogenicity scores produced by the trained classifiers, and generating a pathogenicity table that identifies the average and/or maximum pathogenicity score for each unobserved pSNV in the at least some unobserved pSNVs.

The training further includes applying the trained classifiers to produce pathogenicity scores for at least some observed pSNVs in the common benign set of observed pSNVs, for each observed pSNV in the at least some observed pSNVs, determining an average and/or maximum pathogenicity score from the pathogenicity scores produced by the trained classifiers, and generating the pathogenicity table that identifies the average and/or maximum pathogenicity score for each observed pSNV in the at least some observed pSNVs.

In some implementations, the input promoter sequences are flanked by upstream and downstream reference bases. In some implementations, the reference bases in the input promoter sequences are one-hot encoded.

The classifiers are deep convolutional neural networks that contain groups of residual blocks arranged in a sequence from lowest to highest, each group of residual blocks is parameterized by a number of convolution filters in the residual blocks, a convolution window size of the residual blocks, and an atrous convolution rate of the residual blocks, the atrous convolution rate progresses non-exponentially from a lower residual block group to a higher residual block group, the size of convolution window varies between groups of residual blocks, and each residual block comprises at least one batch normalization layer, at least one rectified linear unit (abbreviated ReLU) layer, at least one atrous convolution layer, and at least one residual connection.

The ensemble includes 4 to 10 deep convolutional neural networks, in one implementation. In another implementation, the ensemble includes 10 to 100 deep convolutional neural networks. In yet another implementation, the ensemble includes 100 to 200 deep convolutional neural networks.

Other implementations may include a non-transitory computer readable storage medium storing instructions executable by a processor to perform functions of the system described above. Yet another implementation may include a method performing the functions of the system described above.

A second neural network-based system implementation of the technology disclosed includes one or more processors coupled to memory. The memory is loaded with computer instructions that implement a trained pathogenicity classifier which predict pathogenicity of promoter region single nucleotide variants (abbreviated pSNVs).

A trained pathogenicity classifier comprises an input module (not shown) that accepts an input promoter sequence with reference bases at positions covering observed pSNVs and substitutionally generated unobserved pSNVs.

The trained pathogenicity classifier also comprises a processing module (not shown) that processes the input promoter sequence through one or more layers of the pathogenicity classifier to generate an alternative representation of the input promoter sequence. In some implementations, when the trained pathogenicity classifier is a deep convolutional neural network, the layers are convolution layers with convolution filters and the alternative representation is a convolved representation. In other implementations, when the trained pathogenicity classifier is a recurrent neural network, the layers are recurrent units with gates and the alternative representation is a hidden representation.

The trained pathogenicity classifier further comprises an output module (not shown) that processes the alternative representation to generate an output which, for each position in the input promoter sequence, classifies each of three base variations from a corresponding reference base as benign or pathogenic. In some implementations, the output includes pathogenicity likelihood scores for each of the three base variations.

The trained pathogenicity classifier receives supplemental input from a protein binding affinity sub-classifier that encodes a protein binding affinity score to each position in the input promoter sequence. The trained pathogenicity classifier also receives supplemental input from a DNA accessibility sub-classifier that encodes a DNA accessibility inducing score to each position in the input promoter sequence.

Other implementations may include a non-transitory computer readable storage medium storing instructions executable by a processor to perform functions of the system described above. Yet another implementation may include a method performing the functions of the system described above.

Any data structures and code described or referenced above are stored according to many implementations on a computer-readable storage medium, which may be any device or medium that can store code and/or data for use by a computer system. This includes, but is not limited to, volatile memory, non-volatile memory, application-specific integrated circuits (ASICs), field-programmable gate arrays (FPGAs), magnetic and optical storage devices such as disk drives, magnetic tape, CDs (compact discs), DVDs (digital versatile discs or digital video discs), or other media capable of storing computer-readable media now known or later developed.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A system comprising:
one or more processors; and
a non-transitory computer readable medium comprising a
trained convolutional neural network-based pathogenicity classifier that predicts pathogenicity of promoter region single nucleotide variants (abbreviated pSNVs)

and instructions that, when executed by the one or more processors, cause the system to perform operations comprising:
accessing an input promoter sequence with reference bases at a plurality of base positions comprising one or more observed pSNV positions corresponding to pSNVs identified within a sample genomic dataset;
processing the input promoter sequence through one or more layers of the trained convolutional neural network-based pathogenicity classifier to generate an alternative representation of the input promoter sequence, the one or more layers of the trained convolutional neural network-based pathogenicity classifier:
trained utilizing input promoter training sequences comprising one or more observed pSNVs sampled from pSNVs identified within the sample genomic dataset and one or more unobserved pSNVs sampled from a pool of substitutionally generated pSNVs at base positions for which pSNVs are not identified within the sample genomic dataset; and
comprising one or more groups of residual blocks, each residual block comprising one or more of a batch normalization layer, a rectified linear unit (ReLU), an atrous convolution layer, or a residual connection; and
processing the alternative representation to generate, for each base position in the input promoter sequence, pathogenicity predictions that classify each of three base variations from a corresponding reference base as benign or pathogenic.

2. The system of claim 1, wherein each residual block comprises a batch normalization layer, a rectified linear unit (ReLU), an atrous convolution layer, and a residual connection.

3. The system of claim 1, wherein the operations further comprise:
encoding, by one or more protein binding affinity sub-classifiers of the trained convolutional neural network-based pathogenicity classifier, a protein binding affinity score to each base position in the input promoter sequence; and
generating the pathogenicity predictions for each of the three base variations at each base position in the input promoter sequence based on the a corresponding protein binding affinity score.

4. The system of claim 1, wherein the operations further comprise:
encoding, by one or more deoxyribonucleic acid (abbreviated DNA) accessibility sub- classifiers, a DNA accessibility inducing score to each base position in the input promoter sequence; and
generating the pathogenicity predictions for each of the three base variations at each base position in the input promoter sequence based on the a corresponding DNA accessibility inducing score.

5. The system of claim 1, wherein, for each of the input promoter training sequences, the one or more sampled observed pSNVs are sampled from a common benign set of observed pSNVs.

6. The system of claim 5, wherein, for each of the input promoter training sequences, sampling of the one or more observed pSNVs and the one or more unobserved pSNVs is weighted to reduce a difference between one or more of a trinucleotide context distribution, a local GC-content distribution, or a sequence coverage distribution between the one or more sampled observed pSNVs and the one or more unobserved pSNVs sampled for each input promoter training sequence.

7. The system of claim 5, wherein the one or more layers of the trained convolutional neural network-based pathogenicity classifier are trained utilizing ground truth data with base-wise and position-wise labels for the input promoter training sequences, the base-wise and position-wise labels comprising:
a benign label for each of the one or more observed pSNVs at a respective base and position thereof; and
a pathogenic label for each of the one or more unobserved pSNVs at a respective base and position thereof.

8. A computer-implemented method comprising:
accessing an input promoter sequence with reference bases at a plurality of base positions comprising one or more observed pSNV positions corresponding to pSNVs identified within a sample genomic dataset;
processing the input promoter sequence through one or more layers of a trained convolutional neural network-based pathogenicity classifier to generate an alternative representation of the input promoter sequence, the one or more layers of the trained convolutional neural network-based pathogenicity classifier:
trained utilizing input promoter training sequences comprising one or more observed pSNVs sampled from pSNVs identified within the sample genomic dataset and one or more unobserved pSNVs sampled from a pool of substitutionally generated pSNVs at base positions for which pSNVs are not identified within the sample genomic dataset; and
comprising one or more groups of residual blocks, each residual block comprising one or more of a batch normalization layer, a rectified linear unit (ReLU), an atrous convolution layer, or a residual connection; and
processing the alternative representation to generate, for each base position in the input promoter sequence, pathogenicity predictions that classify each of three base variations from a corresponding reference base as benign or pathogenic.

9. The computer-implemented method of claim 8, wherein each residual block comprises a batch normalization layer, a rectified linear unit (ReLU), an atrous convolution layer, and a residual connection.

10. The computer-implemented method of claim 8, further comprising:
encoding, by one or more protein binding affinity sub-classifiers of the trained convolutional neural network-based pathogenicity classifier, a protein binding affinity score to each base position in the input promoter sequence; and
generating the pathogenicity predictions for each of the three base variations at each base position in the input promoter sequence based on the a corresponding protein binding affinity score.

11. The computer-implemented method of claim 8, further comprising:
encoding, by one or more deoxyribonucleic acid (abbreviated DNA) accessibility sub- classifiers, a DNA accessibility inducing score to each base position in the input promoter sequence; and
generating the pathogenicity predictions for each of the three base variations at each base position in the input promoter sequence based on the a corresponding DNA accessibility inducing score.

12. The computer-implemented method of claim 8, wherein, for each of the input promoter training sequences, the one or more observed pSNVs are sampled from a common benign set of observed pSNVs.

13. The computer-implemented method of claim 12, wherein, for each of the input promoter training sequences, sampling of the one or more observed pSNVs and the one or more sampled unobserved pSNVs is weighted to reduce a difference between one or more of a trinucleotide context distribution, a local GC-content distribution, or a sequence coverage distribution between the one or more observed pSNVs and the one or more unobserved pSNVs sampled for each input promoter training sequence.

14. The computer-implemented method of claim 12, wherein the one or more layers of the trained convolutional neural network-based pathogenicity classifier are trained utilizing ground truth data with base-wise and position-wise labels for the input promoter training sequences, the base-wise and position-wise labels comprising:
   a benign label for each of the one or more observed pSNVs at a respective base and position thereof; and
   a pathogenic label for each of the one or more unobserved pSNVs at a respective base and position thereof.

15. A non-transitory computer readable medium comprising instructions that, when executed by at least one processor, cause a computing device to perform operations comprising:
   accessing an input promoter sequence with reference bases at a plurality of base positions comprising one or more observed pSNV positions corresponding to pSNVs identified within a sample genomic dataset;
   processing the input promoter sequence through one or more layers of a trained convolutional neural network-based pathogenicity classifier to generate an alternative representation of the input promoter sequence, the one or more layers of the trained convolutional neural network-based pathogenicity classifier:
   trained utilizing input promoter training sequences comprising one or more observed pSNVs sampled from pSNVs identified within the sample genomic dataset and one or more unobserved pSNVs sampled from a pool of substitutionally generated pSNVs at base positions for which pSNVs are not identified within the sample genomic dataset; and
   comprising one or more groups of residual blocks, each residual block comprising one or more of a batch normalization layer, a rectified linear unit (ReLU), an atrous convolution layer, or a residual connection; and
   processing the alternative representation to generate, for each base position in the input promoter sequence, pathogenicity predictions that classify each of three base variations from a corresponding reference base as benign or pathogenic.

16. The non-transitory computer readable medium of claim 15, wherein each residual block comprises a batch normalization layer, a rectified linear unit (ReLU), an atrous convolution layer, and a residual connection.

17. The non-transitory computer readable medium of claim 15, wherein the operations further comprise:
   encoding, by one or more protein binding affinity sub-classifiers of the trained convolutional neural network-based pathogenicity classifier, a protein binding affinity score to each base position in the input promoter sequence;
   encoding, by one or more deoxyribonucleic acid (abbreviated DNA) accessibility sub-classifiers, a DNA accessibility inducing score to each base position in the input promoter sequence; and
   generating the pathogenicity predictions for each of the three base variations at each base position in the input promoter sequence based on the a corresponding protein binding affinity score and the a corresponding DNA accessibility inducing score.

18. The non-transitory computer readable medium of claim 15, wherein, for each of the input promoter training sequences, the one or more observed pSNVs are sampled from a common benign set of observed pSNVs.

19. The non-transitory computer readable medium of claim 18, wherein, for each of the input promoter training sequences, sampling of the one or more observed pSNVs and the one or more unobserved pSNVs is weighted to reduce a difference between one or more of a trinucleotide context distribution, a local GC-content distribution, or a sequence coverage distribution between the one or more observed pSNVs and the one or more unobserved pSNVs sampled for each input promoter training sequence.

20. The non-transitory computer readable medium of claim 18, wherein the one or more layers of the trained convolutional neural network-based pathogenicity classifier are trained utilizing ground truth data with base-wise and position-wise labels for the input promoter training sequences, the base-wise and position-wise labels comprising:
   a benign label for each of the one or more observed pSNVs at a respective base and position thereof; and
   a pathogenic label for each of the one or more unobserved pSNVs at a respective base and position thereof.

* * * * *